United States Patent
Chen et al.

(10) Patent No.: US 7,247,727 B2
(45) Date of Patent: Jul. 24, 2007

(54) AZAINDOLE THIAZOLINONES

(75) Inventors: Shaoqing Chen, Bridgewater, NJ (US);
Achyutharao Sidduri, Livingston, NJ (US)

(73) Assignee: Hoffmann-La Roche Inc., Nutley, NJ (US)

( * ) Notice: Subject to any disclaimer, the term of this patent is extended or adjusted under 35 U.S.C. 154(b) by 113 days.

(21) Appl. No.: 11/243,855

(22) Filed: Oct. 5, 2005

(65) Prior Publication Data

US 2006/0084674 A1    Apr. 20, 2006

Related U.S. Application Data

(60) Provisional application No. 60/618,672, filed on Oct. 14, 2004.

(51) Int. Cl.
*C07D 47/104*    (2006.01)

(52) U.S. Cl. .................................................. 546/113

(58) Field of Classification Search ................. 546/113
See application file for complete search history.

(56) References Cited

FOREIGN PATENT DOCUMENTS

| | | |
|---|---|---|
| WO | WO 96/14843 | 5/1996 |
| WO | WO 97/34876 | 9/1997 |
| WO | WO 99/21845 | 5/1999 |
| WO | WO 03/028724 | 4/2003 |
| WO | WO 2004/0477660 A2 * | 6/2004 |

OTHER PUBLICATIONS

Nasmyth, K., Science, 274, pp. 1643-1645 (1996).
Edgar et al., Science, 274, pp. 1646-1652 (1996).
King et al., Science, 274, pp. 1652-1659(1996).
Stillman, B., Science, 274, pp. 1659-1664 (1996).
Elledge, S. J., Science, 274, pp. 1664-1672 (1996).
Sherr, C. J., Science, 274, pp. 1672-1677 (1996).
Klohs et al., Current Opinion in Biotechnology, 10, pp. 544-549 (1999).
Morgan, D. O., Annu. Rev. Cell Dev. Biol., 13, pp. 216-291 (1997).
Parast et al., Biochemistry, 37, pp. 16788-16801 (1998).
Hennequin et al., J. Med. Chem., 45, pp. 1300-1312 (2002).

* cited by examiner

*Primary Examiner*—D. Margaret Seaman
*Assistant Examiner*—Nizal S. Chandrakumar
(74) *Attorney, Agent, or Firm*—George W. Johnston; Patricia S. Rocha-Tramaloni; David E. Wildman

(57) ABSTRACT

Azaindole thiazolinone derivatives which demonstrate CDK1 and CDK2 antiproliferative activities and are useful as anti-cancer agents.

46 Claims, No Drawings

AZAINDOLE THIAZOLINONES

PRIORITY TO RELATED APPLICATIONS

This application claims the benefit of U.S. Provisional Application No. 60/618,672, filed Oct. 14, 2004, which is hereby incorporated by reference in its entirety.

FIELD OF THE INVENTION

The field of this invention relates to azaindole thiazolinone derivatives which demonstrates CDK1 and CDK2 antiproliferative activity and are useful as anti-cancer agents.

BACKGROUND OF THE INVENTION

Cyclin-dependent kinases (CDKs) are serine-threonine protein kinases that play critical roles in regulating the transitions between different phases of the cell-cycle, such as the progression from a quiescent stage in $G_1$ (the gap between mitosis and the onset of DNA replication for a new round of cell division) to S (the period of active DNA synthesis), or the progression from $G_2$ to M phase, in which active mitosis and cell-division occurs. (See, e.g., the articles compiled in *Science*, 274:1643-1677 (1996); and *Ann. Rev. Cell Dev. Biol.*, 13:261-291 (1997)). CDK complexes are formed through association of a regulatory cyclin subunit (e.g., cyclin A, B1, B2, D1, D2, D3 and E) and a catalytic kinase subunit (e.g., CDK1, CDK2, CDK4, CDK5 and CDK6). As the name implies, the CDKs display an absolute dependence on the cyclin subunit in order to phosphorylate their target substrates, and different kinase/cyclin pairs function to regulate progression through specific phases of the cell-cycle.

As seen above, these protein kinases are a class of proteins (enzymes) that regulate a variety of cellular functions. This is accomplished by the phosphorylation of specific amino acids on protein substrates resulting in conformational alteration of the substrate protein. The conformational change modulates the activity of the substrate or its ability to interact with other binding partners. The enzyme activity of the protein kinase refers to the rate at which the kinase adds phosphate groups to a substrate. It can be measured, for example, by determining the amount of a substrate that is converted to a product as a function of time. Phosphorylation of a substrate occurs at the active-site of a protein kinase.

In view of the above properties, these kinases play an important part in the propagation of growth factor signal transduction that leads to cellular proliferation, differentiation and migration. Fibroblast growth factor (FGF) and vascular endothelial growth factor (VEGF) have been recognized as important mediators of tumor promoted angiogenesis. VEGF activates endothelial cells by signaling through two high affinity receptors, one of which is the kinase insert domain-containing receptor (KDR). (See, Hennequin L. F. et. al., *J. Med. Chem.* 45(6):1300 (2002). FGF activates endothelial cells by signaling through the FGF receptor (FGFR). Solid tumors depend upon the formation of new blood vessels (angiogenesis) to grow. Accordingly, inhibitors of the receptors FGFR and KDR that interfere with the growth signal transduction, and thus slow down or prevent angiogenesis, are useful agents in the prevention and treatment of solid tumors. (See, Klohs W. E. et. al., *Current Opinion in Biotechnology*, 10:544 (1999).

Because CDKs such as CDK1 and CDK2 serve as general activators of cell division, inhibitors of CDK1 and CDK2 can be used as antiproliferative agents. These inhibitors can be used for developing therapeutic intervention in suppressing deregulated cell cycle progression.

SUMMARY OF THE INVENTION

In accordance with this invention, it has been discovered that the compound of the formula:

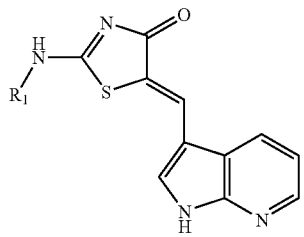

I wherein
R₁ is hydrogen, lower alkyl, hydroxy-lower alkyl, cyclo-lower alkyl, lower alkoxy-lower alkyl or R₂—(X)n; n is an integer from 0 to 1;
X is selected from lower alkylene, hydroxy-loweralkylene, cyclo-loweralkylene, lower alkoxy-lower alkylene and lower alkanoyloxy-lower alkylene;

R₂ is 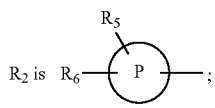

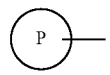

is an aryl ring, a 4 to 6 membered heterocycloalkyl ring containing from 3 to 5 carbon atoms and from 1 to 2 hetero atoms selected from the group consisting of oxygen, nitrogen and sulfur, or a 5 or 6 membered heteroaromatic ring containing from 1 to 2 hetero atoms selected from the group consisting of oxygen, sulfur and nitrogen;
R₅ and R₆ are independently selected from the group consisting of hydroxy, hydroxy-lower alkyl, hydrogen, lower alkyl, halogen, perfluro lower alkyl or lower alkoxy; or
N-oxides of compounds where R₂ contains a nitrogen in the heteroaromatic ring, sulfones where R₂ contains a sulfur in the heterocycloalkyl ring or heteroaromatic ring, or
pharmaceutically acceptable salts thereof, inhibit the activity of CDKs, particularly, CDK1 and CDK2.

These inventive agents and pharmaceutical compositions containing such agents are useful in treating various diseases or disorder states associated with uncontrolled or unwanted cellular proliferation, such as cancer, autoimmune diseases, viral diseases, fungal diseases, neurodegenerative disorders and cardiovascular diseases.

Inhibiting and/or modulating the activity of CDKs, particularly CDK1 and CDK2, makes these compounds of formula I and compositions containing these compounds useful in treating diseases medicated by kinase activity, particularly as anti-tumor agents in treating cancers.

DETAILED DESCRIPTION OF THE INVENTION

As pointed out herein, the compounds of formula I are potential anti-proliferation agents and are useful for mediating and/or inhibiting the activity of CDKs, particularly CDK1, thus providing anti-tumor agents for treatment of cancer or other diseases associated with uncontrolled or abnormal cell proliferation.

Among the preferred compounds of formula I are the compounds of the formula:

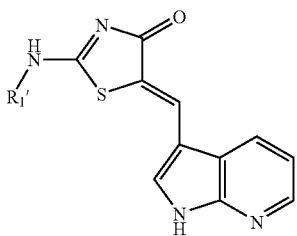

I-A wherein $R_1'$ is hydrogen, lower alkyl, hydroxy lower alkyl, lower alkoxy-lower alkyl or cyclo-lower alkyl; or pharmaceutically acceptable salts thereof and compounds of the formula:

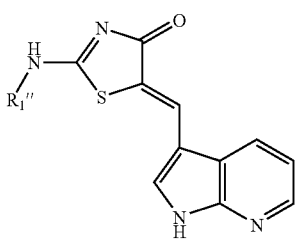

I-B wherein
$R_1''$ is $R_2$—$(X)_n$, and $R_2$, X and n are as above; or
N-oxides of compounds where $R_2$ contains a nitrogen in the heteroaromatic ring, sulfones where $R_2$ contains a sulfur in the heterocycloalkyl ring or heteroaromatic ring; or
pharmaceutically acceptable salts thereof.

In compounds I and I-B, where $R_2$ and X are substituents containing an aryl moiety, the preferred aryl moiety is phenyl. As used herein the halogen includes all four halogens such as chlorine, fluorine, bromine and iodine.

As used in the specification, the term "lower alkyl", alone or in combination, means a monovalent straight or branched-chain saturated hydrocarbon alkyl group containing from one to six carbon atoms, such as methyl, ethyl, n-propyl, isopropyl, n-butyl, sec-butyl, isobutyl, tert-butyl, n-pentyl, n-hexyl and the like.

The term "cycloalkyl" means a cyclolower alkyl substituent which is a monovalent unsubstituted 3- to 6-membered saturated carbocylic hydrocarbon ring. Among the preferred cycloalkyl substituents are cyclopropyl, cyclobutyl, cyclohexyl, etc. with cyclopropyl being especially preferred.

The term "lower alkoxy" means a straight-or branched-chain alkoxy group formed from lower alkyl containing form one to six carbon atoms, such as methoxy, ethoxy, n-propoxy, isopropoxy, n-butoxy, tert-butoxy and the like.

The term "aryl" means a monovalent mono- or bicyclic unsubstituted aromatic hydrocarbon ring, such as phenyl or naphthyl, with phenyl being preferred.

The term "heterocycloalkyl" refers to a 4 to 6 membered monocyclic saturated ring containing 3 to 5 carbon atoms and one or two hetero atoms selected from the group consisting of oxygen, nitrogen or sulfur. Among the preferred heterocyclic alkyl groups are included mopholinyl, thiopyranyl and tetrahydropyranyl.

The term "heteroaromatic ring" refers to a monovalent 5 or 6 membered monocyclic heteroaromatic ring containing from 4 to 5 carbon atoms and from 1 to 2 hetero atoms selected from the group consisting of oxygen, nitrogen or sulfur. Among the preferred heteroaromatic groups are included thiophenyl, thioazolyl pyridinyl, furanyl, etc.

The term "lower alkylene" designates a divalent saturated straight or branch chain hydrocarbon substituent containing from one to six carbon atoms.

The term "lower alkanoyloxy" designates a monovalent residue of a saturated aliphatic carboxylic acid contained from 2 to 6 carbon atoms where the hydrogen atom on the carboxy (—COOH) moiety has been removed. Among the preferred lower alkanoyloxy groups are include acetyloxy, propanoyloxy and butyryloxy.

The term "cyclo lower alkylene" designates a cyclo lower alkenyl substituent which is a divalent unsubstituted 3 to 6 membered saturated carbocyclic hydrocarbon ring. Among the preferred cycloalkylene substituents are cyclopropenyl and cyclobutenyl.

The term "lower alkanoyloxy lower alkylene" designates a lower alkylene substituent substituted, preferably monosubstituted, with a lower alkanoyloxy group where lower alkanoyloxy is defined as above.

The term "lower alkoxy-lower alkylene" denotes a lower alkylene substituent, as designated hereinbefore, substituted, preferably monosubstituted, with a lower alkoxy group, where lower alkoxy is defined as above.

The term "hydroxy lower alkylene" designates a lower alkylene substituent substituted, preferably monosubstituted, with a hydroxy group.

The term "aryloxy" designates an aryloxy substituent where aryl is as above. The preferred aryl group is phenyl and the preferred aryloxy is phenoxy.

The term "perfluoro-lower alkyl" means any lower alkyl group wherein all the hydrogens of the lower alkyl group are substituted or replaced by fluorine. Among the preferred perfluoro-lower alkyl groups are trifluoromethyl, pentafluoroethyl, heptafluoropropyl, etc with trifluromethyl being especially preferred.

The term "pharmaceutically acceptable salts" refers to conventional acid-addition salts or base-addition salts that retain the biological effectiveness and properties of the compounds of formulae I, I-A and I-B are formed from suitable non-toxic organic or inorganic acids, or organic or inorganic bases. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Sample base-addition salts include those derived from ammonium, potassium, sodium and, quaternary ammonium hydroxides, such as for example, tetramethylammonium hydroxide. The chemical modification of a pharmaceutical compound (i.e., drug) into a salt is a technique well known to pharmaceutical chemists to obtain improved physical and chemical stability, hygroscopicity, flowability and solubility of compounds. See, e.g., H. Ansel et al., *Pharmaceutical Dosage Forms and Drug Delivery Systems* (6th Ed. 1995) at pp. 196 and 1456-1457.

In accordance with this invention, the compounds of formula I can be prepared from a compound of the formula:

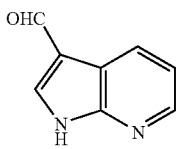

II

The compound of formula II is converted to the compound of formula I via the following reaction scheme.

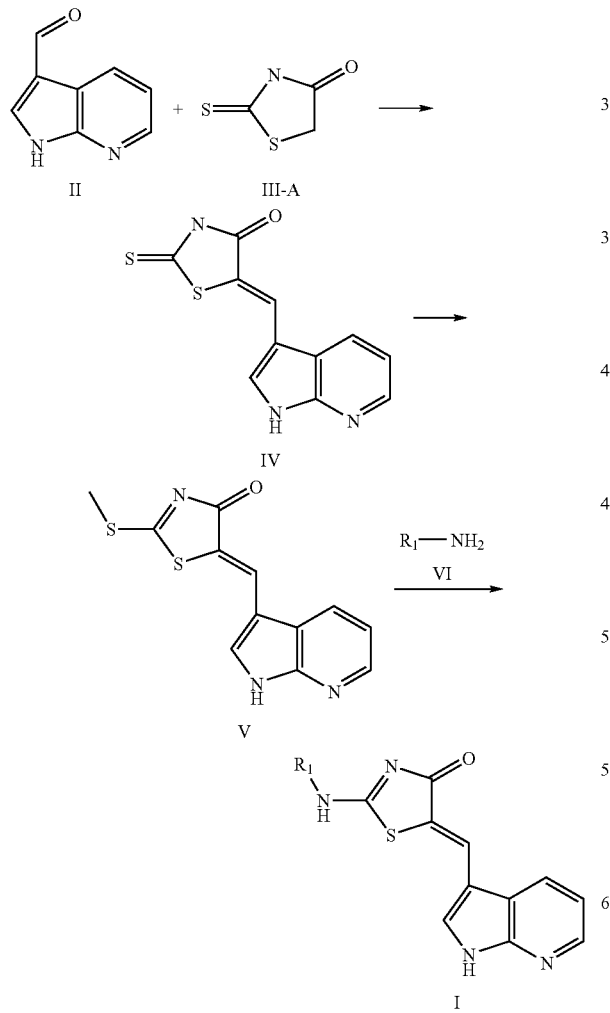

wherein $R_1$ is as above.

In accordance with this invention, the compound of formula II is reacted with the compound of formula III-A [rhodanine(2-thio-4-thiazolin-4-one)] via a Knoevenegel reaction to produce the compound of formula IV. Any of the conditions conventional in carrying out Knoevenegel reaction can be utilized in carrying out this condensation. Generally, this reaction is carried out at reflux temperature in the presence of alkali metal acetate and acetic acid. In the next step of this synthesis, the resulting substituted thiazolidine of formula IV is treated with a methylating agent to methylate the thio group on the compound of formula IV to produce the compound of formula V. The preferred methylating agent is iodomethane. This reaction is carried out in an organic amine base such as diisopropylethylamine (DIEA). In carrying out this reaction, temperature and pressure are not critical and this reaction can be carried out at room temperature and atmospheric pressure. In fact in carrying out this reaction, any of the conditions conventional in methylating a thio group can be used.

In the next step of this synthesis, the compound of formula V is reacted with the compound of formula VI to produce the compound of formula I. The compound of formula VI is an amine and any means conventionally used in amine substitution of methylthio group can be used in carrying out this reaction. In accordance with one embodiment this substitution is carried out by reacting the compound of formula VI with the compound of formula V in the presence of a conventional solvent such as acetonitrile. Generally, this reaction is carried out in the presence of an amine base such as diisopropylethylamine.

On the other hand, the compound of formula I can be prepared by reacting the compound of formula II with a compound of the formula:

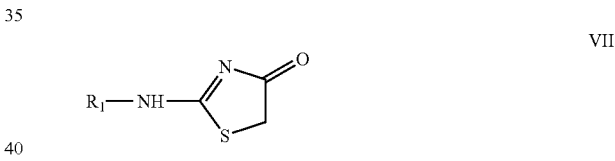

VII wherein $R_1$ is as above.

The reaction of the compound of formula VII with the compound of formula II to produce the compound of formula I, is carried out in a high boiling organic solvent such as benzene or toluene at high temperature of from 50° C. to 200° C. in a closed system. In this manner, this reaction is carried out under high temperatures and pressure. In addition, this reaction is ideally suited to produce compound of Formula I where $R_1$ is hydrogen. The compound of formula VII can be directly formed by direct replacement thorough reacting the compound of the formula $R_1$—$NH_2$     VI wherein $R_1$ is as above, with a compound of the formula III-A. The replacement reaction is generally carried out in the presence of an activator for the thienyl group in the thienyl compound of formula IX and in the presence of an amine base. Among the preferred activators is mercuric chloride. This reaction is carried out in an inert organic solvent. Any conventional inert organic solvent such as acetonitrile, methylene chloride, etc. can be utilized. In carrying out this reaction, an amine base, such as diisoproprylethylamine, is used. In carrying out this reaction, temperature and pressure are not critical and this reaction can be carried out at room temperature and atmospheric pressure. In carrying out this reaction, any conventional method of replacing a thienyl group with an amine can be utilized.

In the compound of formula VI where $R_1$ is X, n is 1 and X is a hydroxy lower alkylene, these compounds can be prepared from the corresponding amino acids or amino acid esters by reduction with an alkali metal borohydride. On the other hand, these hydroxy lower alkylene compounds can be prepared for the corresponding cyano carboxylic acid esters by reduction with lithium aluminum hydride. Reduction reduces the cyano group to an amino group and the ester to a hydroxy group. This reduction should take place before reacting the compound of formula VI with the compound of formula V.

Where the ring ⓟ is an N-oxide of a nitrogen atom in a nitrogen containing ring which forms the rings ⓟ, these N-oxides can be formed from a tertiary ring nitrogen atom by oxidation. Any conventional method of oxidizing a tertiary nitrogen atom to an N-oxide can be utilized. The preferred oxidizing agent is metachloroperbenzoic acid (MCPBA).

The compound of formula I-A includes compounds wherein $R_1'$ is hydrogen. Another class of compounds of the compounds of formula 1A is those compounds where $R_1'$ is cyclo lower alkyl, preferably cyclopropyl. Another class of compounds of the compounds of formula 1A are these compounds where $R_1'$ is hydroxy lower alkyl or lower alkoxy lower alkyl with hydroxy lower alkyl being especially preferred.

In the compounds of formula I-B, where $R_1''$ is $R_2$—$(X)_n$, n can be 0 or 1. Where n is 0. a preferred class of compounds are those compounds where ⓟ is phenyl. The preferred class of compounds where n is 0 and $R_2$ is phenyl are those compounds where $R_5$ and $R_6$ are either both hydrogen or one of $R_5$ and $R_6$ is hydrogen and the other is lower alkoxy or lower alkyl.

On the other hand, another preferred class of compounds of formula I-B are those where $R_1''$ is $R_2$—$(X)_n$ and n is 1. Included within this class of compounds are those compounds where X is cyclo lower alkylene, preferably cyclopropylene. With respect to this class of compound wherein n is 1 and X is cyclolower alkylene, are included those compounds where ⓟ is phenyl and are $R_5$ and $R_6$ are both hydrogen or one of $R_5$ and $R_6$ is hydrogen and the other is lower alkyl. Another class of the compounds of formula I-B where $R_2$ is phenyl are those compounds where $R_5$ and $R_6$ are hydrogen or halogen with at least one of $R_5$ and $R_6$ being halogen. Another class of compounds of formula I-B where n is 1 are those compounds where X is lower alkanoyloxy lower alkylene. With respect to this class of compounds where $R_1''$ is $R_2$—$(X)_n$ and n is 1 and X is lower alkanoyloxy lower alkylene, are those compounds where $R_2$ is

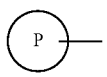

and ⓟ is phenyl, are these compounds where both $R_5$ and $R_6$ are hydrogen or one of $R_5$ and $R_6$ is hydrogen and the other is lower alkenyl or halogen. In accordance with another embodiment of invention are those preferred compounds of formula I-B where n is 1 and X is lower alkenyl. Among the preferred embodiments of this class of compounds are the compounds where $R_2$ is ⓟ and the

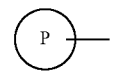

is phenyl. With respect to this embodiment of the invention, the preferred embodiments are those compounds where $R_5$ and $R_6$ are both hydrogen, or $R_5$ and $R_6$ are hydrogen or lower alkyl or halogen with at least one of $R_5$ and $R_6$ being other than hydrogen. Another class of compounds of formula I-B where n is 1 and X is lower alkylene are those compounds where ⓟ is a heteroaromatic ring containing from 1 to 2 hetero atoms selected from the group consisting of oxygen, nitrogen and sulfur. Among the preferred compounds of the class of compounds where

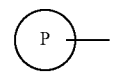

is a hetroaromatic ring are those hetero aromatic rings which contain 1 hetero atom preferably sulfur. In this case, $R_5$ and $R_6$ can both be hydrogen or one of $R_5$ and $R_6$ can be hydrogen and the other halogen or lower alkyl.

In another class of compounds of formula I-B where n is 1 are those compounds where X is hydroxy lower alkylene. With respect to this class of compounds where X is hydroxy lower alkylene are those compounds where

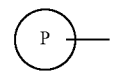

is a phenyl ring. Included within this preferred class of compounds are those compounds where $R_5$ and $R_6$ are both hydrogen and those compounds where $R_5$ and $R_6$ are hydrogen lower alkyl, lower alkoxy or halogen with at least one of $R_5$ and $R_6$ being other than hydrogen.

Pharmaceutical compositions according to the invention may, alternatively or in addition to a compound of Formula I, comprise as an active ingredient pharmaceutically acceptable prodrugs, pharmaceutically active metabolites, and pharmaceutically acceptable salts of such compounds and metabolites. Such compounds, prodrugs, multimers, salts, and metabolites are sometimes referred to herein collectively as "active agents" or "agents."

In the case of agents that are solids, it is understood by those skilled in the art that the inventive compounds and salts may exist in different crystal or polymorphic forms, all of which are intended to be within the scope of the present invention and specified formulas.

Therapeutically effective amounts of the active agents of the invention may be used to treat diseases mediated by modulation or regulation of the protein kinases CDK1. An "effective amount" is intended to mean that amount of an agent that significantly inhibits proliferation and/or prevents de-differentiation of a eukaryotic cell, e.g., a mammalian, insect, plant or fungal cell, and is effective for the indicated utility, e.g., specific therapeutic treatment.

The amount of a given agent that will correspond to such an amount will vary depending upon factors such as the particular compound, disease condition and its severity, the identity (e.g., weight) of the subject or host in need of treatment, but can nevertheless be routinely determined in a manner known in the art according to the particular circumstances surrounding the case, including, e.g., the specific agent being administered, the route of administration, the condition being treated, and the subject or host being treated. "Treating" is intended to mean at least the mitigation of a disease condition in a subject such as mammal (e.g., human), that is affected, at least in part, by the activity of CDK1 protein kinase includes: preventing the disease condition from occurring in a mammal, particularly when the mammal is found to be predisposed to having the disease condition but has not yet been diagnosed as having it; modulating and/or inhibiting the disease condition; and/or alleviating the disease condition. The present invention is further directed to methods of modulating or inhibiting protein kinase CDK1 activity, for example in mammalian tissue, by administering the inventive agent. The activity of agents as anti-proliferatives is easily measured by known methods, for example by using whole cell cultures in an MTT assay. The activity of the inventive agents as modulators of CDK1 protein kinase activity may be measured by any of the methods available to those skilled in the art, including in vivo and/or in vitro assays. Examples of suitable assays for activity measurements include those described in International Publication No. WO 99/21845; Parast et al., Biochemistry, 37, 16788-16801 (1998); Connell-Crowley and Harpes, Cell Cycle: Materials and Methods, (Michele Pagano, ed. Springer, Berlin, Germany) (1995); International Publication No. WO 97/34876; and International Publication No. WO 96/14843. These properties may be assessed, for example, by using one or more of the biological testing procedures set out in the examples below.

The active agents of the invention may be formulated into pharmaceutical compositions as described below. Pharmaceutical compositions of this invention comprise an effective modulating, regulating, or inhibiting amount of a compound of formula I and an inert, pharmaceutically acceptable carrier or diluent. In one embodiment of the pharmaceutical compositions, efficacious levels of the inventive agents are provided so as to provide therapeutic benefits involving anti-proliferative ability. By "efficacious levels" is meant levels in which proliferation is inhibited, or controlled. These compositions are prepared in unit-dosage form appropriate for the mode of administration, e.g., parenteral or oral administration.

An inventive agent can be administered in conventional dosage form prepared by combining a therapeutically effective amount of an agent (e.g., a compound of formula I) as an active ingredient with appropriate pharmaceutical carriers or diluents according to conventional procedures. These procedures may involve mixing, granulating and compressing or dissolving the ingredients as appropriate to the desired preparation.

The pharmaceutical carrier employed may be either a solid or liquid. Exemplary of solid carriers are lactose, sucrose, talc, gelatin, agar, pectin, acacia, magnesium stearate, stearic acid and the like. Exemplary of liquid carriers are syrup, peanut oil, olive oil, water and the like. Similarly, the carrier or diluent may include time-delay or time-release material known in the art, such as glyceryl monostearate or glyceryl distearate alone or with a wax, ethylcellulose, hydroxypropylmethylcellulose, methyl methacrylate and the like.

A variety of pharmaceutical forms can be employed. Thus, if a solid carrier is used, the preparation can be tableted, placed in a hard gelatin capsule in powder or pellet form or in the form of a troche or lozenge. The amount of solid carrier may vary. If a liquid carrier is used, the preparation will be in the form of syrup, emulsion, soft gelatin capsule, sterile injectable solution or suspension in an ampoule or vial or non-aqueous liquid suspension.

To obtain a stable water-soluble dose form, a pharmaceutically acceptable salt of an inventive agent can be dissolved in an aqueous solution of an organic or inorganic acid. If a soluble salt form is not available, the agent may be dissolved in a suitable cosolvent or combinations of cosolvents.

It will be appreciated that the actual dosages of the agents used in the compositions of this invention will vary according to the particular complex being used, the particular composition formulated, the mode of administration and the particular site, host and disease being treated. Optimal dosages for a given set of conditions can be ascertained by those skilled in the art using conventional dosage determination tests in view of the experimental data for an agent.

The compositions of the invention may be manufactured in manners generally known for preparing pharmaceutical compositions, e.g., using conventional techniques such as mixing, dissolving, granulating, dragee-making, levigating, emulsifying, encapsulating, entrapping or lyophilizing. Pharmaceutical compositions may be formulated in a conventional manner using one or more physiologically acceptable carriers, which may be selected from excipients and auxiliaries that facilitate processing of the active compounds into preparations which can be used pharmaceutically.

For oral administration, the compounds can be formulated readily by combining the compounds with pharmaceutically acceptable carriers known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained using a solid excipient in admixture with the active ingredient (agent), optionally grinding the resulting mixture, and processing the mixture of granules after adding suitable auxiliaries, if desired, to obtain tablets or dragee cores.

EXAMPLES

Example 1

5-[1-(1H-Pyrrolo[2,3-b]pyridin-3-yl)-meth-(Z)-ylidine]-2-[(thiophen-2-yl methyl)-amino]-thiazol-4-one

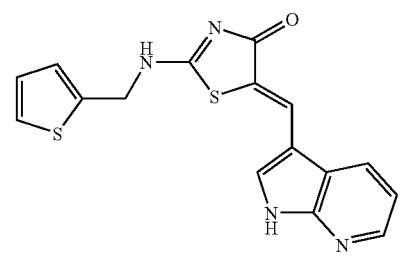

a) Preparation of 3-bromo-1H-pyrrolo[2,3-b]pyridine

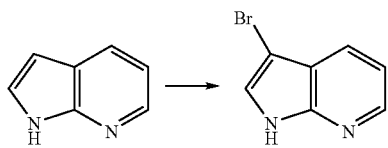

To a solution of 7-azaindole (5 g, 42.2 mmol) in THF (400 mL) were added first the solid N-bromosuccinimide (8 g, 45.0 mmol) then 20 drops of conc. sulfuric acid at room temperature. While stirring some suspension was formed during 2 days. The mixture was diluted with saturated ammonium chloride solution and the two layers were separated. The aqueous layer was extracted with ethyl acetate (4×150 mL). The combined organic extracts were washed with brine solution and dried over anhydrous magnesium sulfate. Filtration of the drying agent and removal of the solvent under the vacuum gave the crude yellow solid. This solid was dissolved in ethyl acetate (~100 mL) at hot condition and then stored in the refrigerator overnight. The solids were collected by filtration and washed with ethyl acetate. After drying in air, 6.2 g (75% yield) of 3-bromo-1H-pyrrolo[2,3-b]pyridine was isolated as an yellow solid: EI-HRMS m/e calcd for $C_7H_5BrN_2$ (M$^+$) 195.9636. found 195.9636.

b) Preparation of 1H-pyrrolo[2,3-b]pyridine-3-carbaldehyde

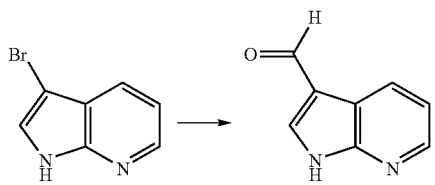

To a suspension of 3-bromo-1H-pyrrolo[2,3-b]pyridine (9.85 g, 50.0 mmol) in THF (300 mL) was added dropwise a 2.5M solution of n-butyllithium in hexanes (42 mL, 105.0 mmol, 2.1 equiv.) at −70° C. The temperature of the reaction mixture was raised to −60° C. during the addition and became a clear solution. The resulting brick red color solution was slowly allowed to warm to −10° C. during a period of 1 h and then stirred for 4 h at this temperature. Again, the mixture was cooled to −70° C. and a solution of dimethylformamide (8.5 mL, 110.0 mmol) in THF (30 mL) was added dropwise. After addition, the mixture was allowed to warm to room temperature and stirred for 15 h. Then, the mixture was diluted with saturated ammonium chloride solution and the two layers were separated. The aqueous layer was extracted with ethyl acetate (2×150 mL). The combined organic extracts were washed with brine solution and dried over anhydrous magnesium sulfate. Filtration of the drying agent and removal of the solvent under the vacuum gave the crude brown solid which was dissolved in ethyl acetate (~70 mL) at hot condition and then stored in the refrigerator overnight. The solids were collected by filtration and washed with ethyl acetate. After drying in air, 6.05 g (83% yield) of 1H-pyrrolo[2,3-b]pyridine-3-carbaldehyde was isolated as an yellow solid: EI-HRMS m/e calcd for $C_8H_6N_2O$ (M$^+$) 146.0480. found 146.0478.

c) One Step Preparation of 1H-pyrrolo[2,3-b]pyridine-3-carbaldehyde

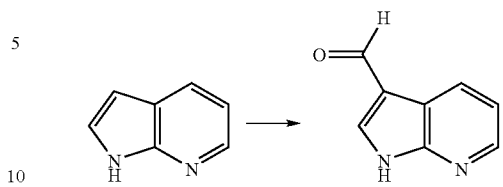

To a suspension of 1H-pyrrolo[2,3-b]pyridine (11.80 g, 100 mmol) in water containing 33% acetic acid (200 mL) was added hexamethylenetetramine (16.8 g, 120 mmol) at room temperature. This solution was heated to 110-120° C. (oil bath temperature) and stirred for 15 h. Then, the reaction mixture was cooled to room temperature and during this period lot of solids were formed. This suspension was poured into a beaker (2 L) containing an ice and the flask has rinsed with water (50 mL). This was then neutralized with saturated sodium bicarbonate solution slowly. After neutralization, the solids were collected by filtration and washed with water. After drying in air, 9.5 g (65% yield) of 1H-pyrrolo[2,3-b]pyridine-3-carbaldehyde was isolated as a white solid: EI-HRMS m/e calcd for $C_8H_6N_2O$ (M$^+$) 146.0480. found 146.0478.

d) Preparation of 2-[(thiophen-2-yl-methyl)-amino]-thiazol-4-one

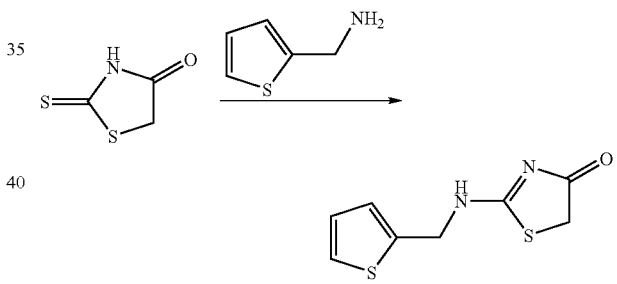

To a suspension of thiophen-2-yl-methylamine (22.63 g, 200 mmol) and Rhodanine (13.32 g, 100 mmol) in acetonitrile (200 mL) was added diisopropylethylamine (DIPEA) (34.8 mL, 45.0 mmol) at room temperature. Then, within 2 min it gave a clear solution and this solution was cooled to 0° C. To this, mercuric chloride (27.15 g, 100 mmol) was added in three portions within a period of 15 min. After addition, the suspension was allowed to warm to room temperature and stirred for 2 days. The resulting black solids were filtered through a plug of celite and washed with dichloromethane (500 mL) and methanol (1.0 L). The combined solvents were removed under the vacuum and the crude residue was diluted with water (250 mL) and ethyl acetate (250 mL). The two layers were separated and the aqueous layer was extracted with dichloromethane (2×250 mL). The two organic extracts were washed separately with brine solution and dried over anhydrous magnesium sulfate. Filtration of the drying agent and removal of the solvent under the vacuum gave the crude solid. This solid was dissolved in acetonitrile (~100 mL) at hot condition and then stored in the refrigerator overnight. The solids were collected by filtration and washed with cold acetonitrile. After drying in air, 12.32 g (58% yield) of 2-[(thiophen-2-yl methyl)-amino]-thiazol-4-one was isolated as a white amorphous solid: EI-HRMS m/e calcd for $C_8H_8N_2OS_2$ (M+) 212.0078. found 212.0083.

e) Preparation of 5-[1-(1H-pyrrolo[2,3-b]pyridin-3-yl)-meth-(Z)-ylidine]-2-[(thiophen-2-yl methyl)-amino]-thiazol-4-one

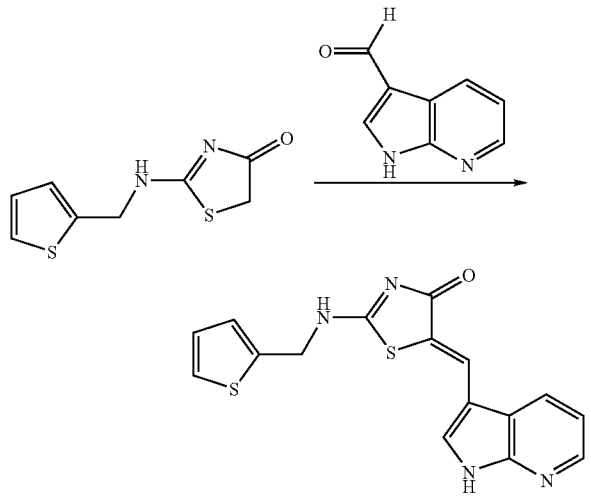

To a suspension of 2-[(thiophen-2-yl methyl)-amino]-thiazol-4-one (225 mg, 1.06 mmol) and 1H-pyrrolo[2,3-b]pyridine-3-carbaldehyde (193.6 mg, 1.35 mmol) in toluene (2 mL) in a microwave tube was added benzoic acid (13 mg, 0.11 mmol) and piperidine (11 uL, 0.11 mmol) at room temperature. The microwave tube was sealed and heated to 150° C. in a closed microwave for 1 h. Then, the mixture was cooled to room temperature and diluted with toluene. The solids were collected by filtration and washed with toluene. After drying in air, 330 mg (91.5% yield) of 5-[1-(1H-pyrrolo[2,3-b]pyridin-3-yl)-meth-(Z)-ylidine]-2-[(thiophen-2-yl methyl)-amino]-thiazol-4-one was isolated as a off-white solid: mp 243-246° C.; HRES(+) m/e calcd for $C_{16}H_{12}N_4OS_2$ (M+H)+ 341.0526. found 341.0528.

Example 2

5-[1-(1H-Pyrrolo[2,3-b]pyridin-3-yl)-meth-(Z)-ylidine]-2-[(thiophen-2-yl methyl)-amino]-thiazol-4-one hydrochloride salt

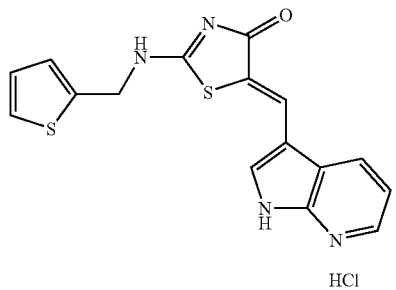

HCl

To a suspension of 5-[1-(1H-pyrrolo[2,3-b]pyridin-3-yl)-meth-(Z)-ylidine]-2-[(thiophen-2-yl methyl)-amino]-thiazol-4-one (50 mg, 0.15 mmol) in methanol (2 mL) was added dropwise trimethylchlorosilane (19 uL, 0.15 mmol) at room temperature. The mixture gave a clear solution after 1 h and stirred for another 2 h. Then, the mixture was diluted with t-butyl methyl ether (10 mL). The resulting solids were collected by filtration and washed with t-butyl methyl ether. After drying in air, 40 mg (73% yield) of 5-[1-(1H-pyrrolo[2,3-b]pyridin-3-yl)-meth-(Z)-ylidine]-2-[(thiophen-2-yl methyl)-amino]-thiazol-4-one as hydrochloride salt was isolated as an amorphous solid: HRES(+) m/e calcd for $C_{16}H_{12}N_4OS_2$ (M+H)+ 341.0526. found 341.0528.

Example 3

2-(2-Hydroxy-1-(R)-phenyl-ethylamino)-5-[1-(1H-pyrrolo[2,3-b]pyridin-3-yl)-meth-(Z)-ylidine]-thiazol-4-one

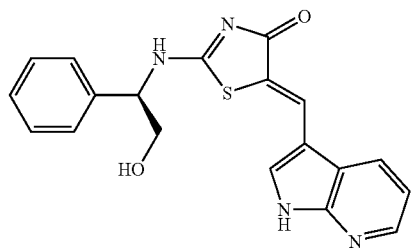

a) Preparation of 2-(2-(R)-hydroxy-1-phenyl-ethylamino)-thiazol-4-one

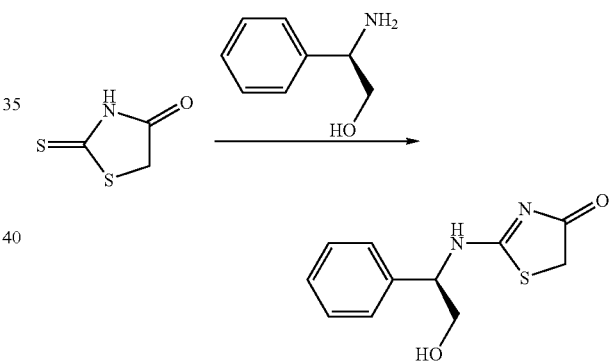

To a suspension of (R)-(−)-2-phenylglycinol (15.34 g, 111.82 mmol) and Rhodanine (14.65 g, 110 mmol) in acetonitrile (200 mL) was added DIPEA (20.03 mL, 115 mmol) at room temperature. Then, it gave a clear solution within 2 min and this solution was cooled to 0° C. To this, mercuric chloride (31.22 g, 115 mmol) was added in three portions within a period of 15 min. After addition, the suspension was allowed to warm to room temperature and stirred for 2 days. The resulting black solids were filtered through a plug of celite and washed with dichloromethane (500 mL) and methanol (1.0 L). The combined solvents were removed under the vacuum and the crude residue was diluted with water (250 mL) and ethyl acetate (250 mL). The two layers were separated and the aqueous layer was extracted with dichloromethane (2×250 mL). The two organic extracts were washed separately with brine solution and dried over anhydrous magnesium sulfate. Filtration of the drying agent and removal of the solvent under the vacuum gave the crude yellow solid. This solid was dissolved in acetonitrile (~100 mL) at hot condition and then stored in the refrigerator overnight. The solids were collected by filtration and washed with cold acetonitrile (20 mL). After drying in air, 12.99 g (50% yield) of 2-(2-(R)-hydroxy-1-phenyl-ethylamino)-thiazol-4-one was isolated as a white amorphous solid: EI-HRMS m/e calcd for $C_{11}H_{12}N_2O_2S$ (M–$H_2O$) 218.0514. found 218.0511.

b) Preparation of 2-(2-hydroxy-1-(R)-phenyl-ethylamino)-5-[1-(1H-pyrrolo[2,3-b]pyridin-3-yl)-meth-(Z)-ylidine]-thiazol-4-one

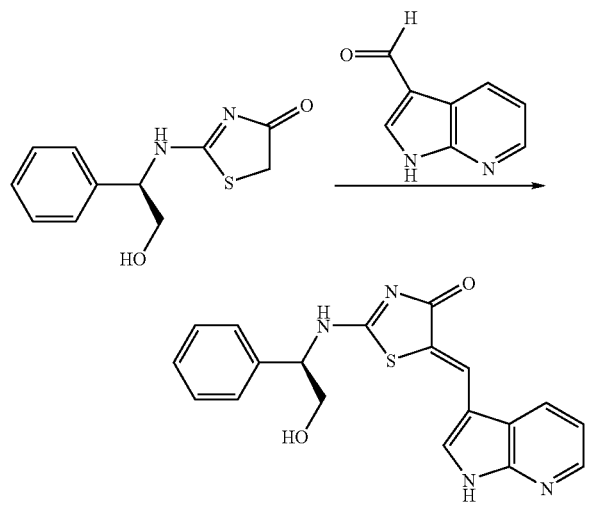

To a suspension of 2-(2-(R)-hydroxy-1-phenyl-ethylamino)-thiazol-4-one (100 mg, 0.43 mmol) and 1H-pyrrolo[2,3-b]pyridine-3-carbaldehyde (77.3 mg, 0.53 mmol) in toluene (2 mL) in a microwave tube was added benzoic acid (5.2 mg, 0.043 mmol) and piperidine (4.3 uL, 0.043 mmol) at room temperature. The microwave tube was sealed and heated to 150° C. in a closed microwave for 1 h. Then, the mixture was cooled to room temperature and diluted with toluene. The solids were collected by filtration and washed with toluene. After drying in air, 135 mg (87.5% yield) of 2-(2-hydroxy-1-(R)-phenyl-ethylamino)-5-[1-(1H-pyrrolo[2,3-b]pyridin-3-yl)-meth-(Z)-ylidine]-thiazol-4-one was isolated as an yellow solid: mp 317-319° C.; HRES(+) m/e calcd for $C_{16}H_{12}N_4OS_2$ (M+H)$^+$ 365.1067. found 365.1070.

Example 4

2-(3-Chloro-4-fluorobenzylamino)-5-[1-(1H-pyrrolo[2,3-b]pyridin-3-yl)-meth-(Z)-ylidine]-thiazol-4-one

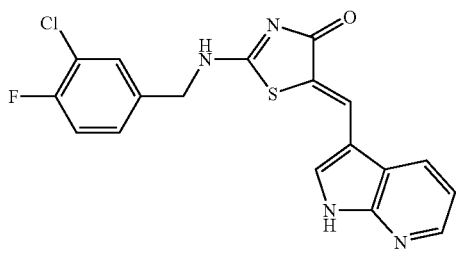

a) Preparation of 2-(3-chloro-4-fluorobenzylamino)-thiazol-4-one

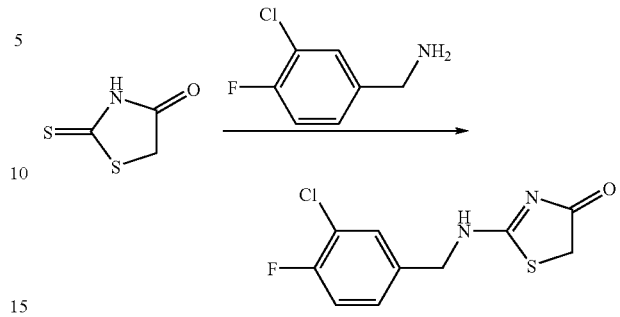

To a suspension of 3-chloro-4-fluorobenzylamine (2.5 g, 15.66 mmol) and Rhodanine (2 g, 15 mmol) in acetonitrile (50 mL) was added DIPEA (5.57 mL, 32 mmol) at room temperature. Then, this solution was cooled to 0° C. and mercuric chloride (4.34 g, 16 mmol) was added in two portions within a period of 10 min. After addition, the suspension was allowed to warm to room temperature and stirred for 2 days. The resulting black solids were filtered through a plug of celite and washed with dichloromethane (200 mL) and methanol (500 mL). The combined solvents were removed under the vacuum and the crude residue was diluted with water (150 mL) and ethyl acetate (150 mL). The two layers were separated and the aqueous layer was extracted with ethyl acetate (2×100 mL). The combined organic extracts were washed with brine solution and dried over anhydrous magnesium sulfate. Filtration of the drying agent and removal of the partial solvent under the vacuum gave lot of solids. After cooling in the refrigerator, the solids were collected by filtration and washed with cold ethyl acetate. After drying in air, 2.5 g (64% yield) of 2-(3-chloro-4-fluorobenzylamino)-thiazol-4-one was isolated as a white amorphous solid: EI-HRMS m/e calcd for $C_{10}H_8ClFN_2OS$ (M$^+$) 258.0030. found 258.0029.

b) Preparation of 2-(3-chloro-4-fluorobenzylamino)-5-[1-(1H-pyrrolo[2,3-b]pyridin-3-yl)-meth-(Z)-ylidine]-thiazol-4-one

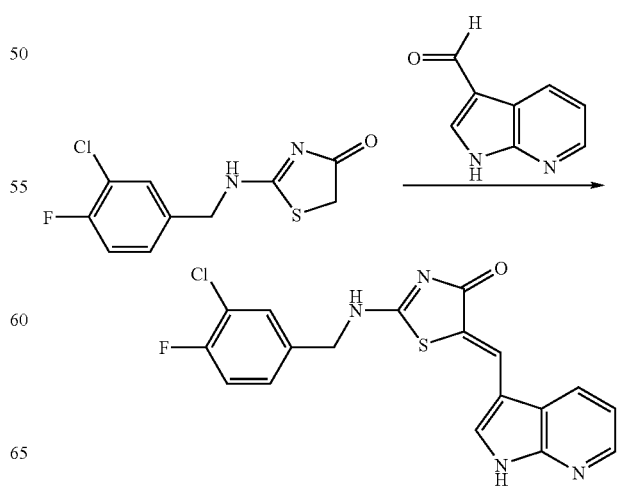

To a suspension of 2-(3-chloro-4-fluorobenzylamino)-thiazol-4-one (100 mg, 0.39 mmol) and 1H-pyrrolo[2,3-b]pyridine-3-carbaldehyde (71 mg, 0.48 mmol) in toluene (2 mL) in a microwave tube was added benzoic acid (4.8 mg, 0.39 mmol) and piperidine (3.9 uL, 0.039 mmol) at room temperature. The microwave tube was sealed and heated to 150° C. in a closed microwave for 1 h. Then, the mixture was cooled to room temperature and diluted with toluene. The solids were collected by filtration and washed with toluene. After drying in air, 145 mg (97% yield) of 2-(3-chloro-4-fluorobenzylamino)-5-[1-(1H-pyrrolo[2,3-b]pyridin-3-yl)-meth-(Z)-ylidine]-thiazol-4-one was isolated as an yellow solid: mp 318-320° C.; HRES(+) m/e calcd for $C_{16}H_{12}N_4OS_2$ $(M+H)^+$ 387.0477. found 387.0477.

Example 5

2-((1R,2S)-2-Phenyl-cyclopropylamino)-5-[1-(1H-pyrrolo[2,3-b]pyridin-3-yl)-meth-(Z)-ylidine]-thiazol-4-one

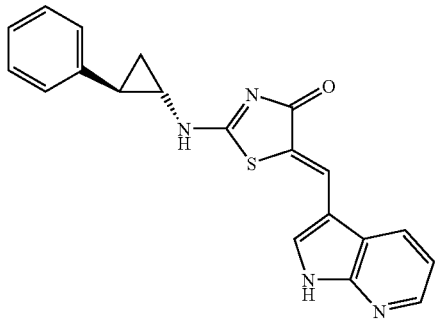

a) Preparation of 2-((1R,2S)-2-phenyl-cyclopropylamino)-thiazol-4-one

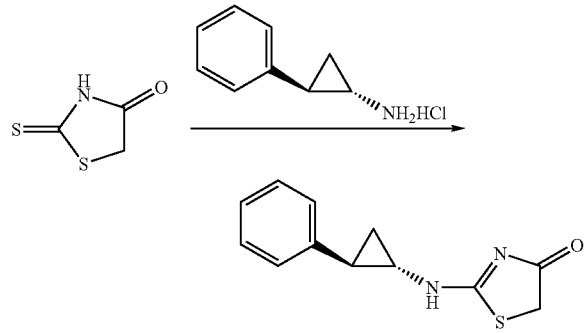

To a suspension of (1R,2S)-2-phenyl-cyclopropylamine hydrochloride (0.85 g, 5 mmol) and Rhodanine (0.68 g, 5 mmol) in acetonitrile (20 mL) was added DIPEA (2.61 mL, 15 mmol) at room temperature. Then, this solution was cooled to 0° C. and mercuric chloride (1.35 g, 5 mmol) was added in two portions within a period of 10 min. After addition, the suspension was allowed to warm to room temperature and stirred for 2 days. The resulting black solids were filtered through a plug of celite and washed with ethyl acetate (500 mL). The solvent was removed under the vacuum and the crude residue was diluted with water (100 mL) and ethyl acetate (100 mL). The two layers were separated and the aqueous layer was extracted with ethyl acetate (2×100 mL). The combined organic extracts were washed with brine solution and dried over anhydrous magnesium sulfate. Filtration of the drying agent and removal of the solvent under the vacuum gave the crude residue which was purified by using a Biotage silica gel column chromatography to obtain 0.474 g (42% yield) of 2-((1R,2S)-2-phenyl-cyclopropylamino)-thiazol-4-one was isolated as a white amorphous solid: EI-HRMS m/e calcd for $C_{12}H_{12}N_2OS$ $(M^+)$ 232.0670. found 232.0665.

b) Preparation of 2-((1R,2S)-2-phenyl-cyclopropylamino)-5-[1-(1H-pyrrolo[2,3-b]pyridin-3-yl)-meth-(Z)-ylidine]-thiazol-4-one

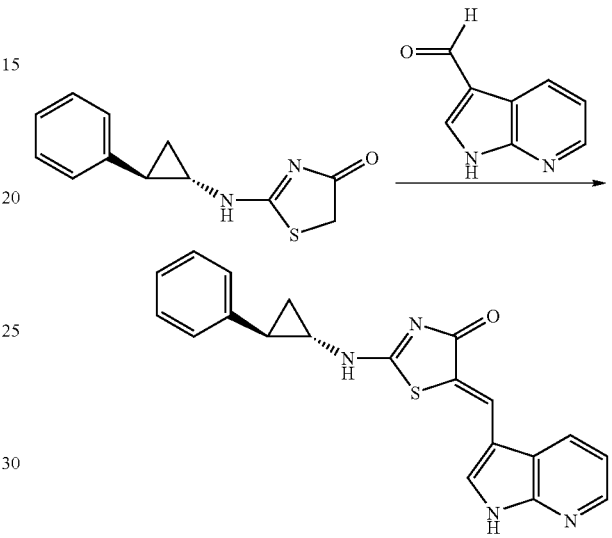

To a suspension of 2-((1R,2S)-2-phenyl-cyclopropylamino)-thiazol-4-one (225 mg, 1.06 mmol) and 1H-pyrrolo[2,3-b]pyridine-3-carbaldehyde (193.6 mg, 1.35 mmol) in toluene (2 mL) in a microwave tube was added benzoic acid (13 mg, 0.11 mmol) and piperidine (11 uL, 0.11 mmol) at room temperature. The microwave tube was sealed and heated to 150° C. in a closed microwave for 1 h. Then, the mixture was cooled to room temperature and diluted with toluene. The solids were collected by filtration and washed with toluene. After drying in air, 330 mg (91.5% yield) of 2-((1R,2S)-2-phenyl-cyclopropylamino)-5-[1-(1H-pyrrolo[2,3-b]pyridin-3-yl)-meth-(Z)-ylidine]-thiazol-4-one was isolated as a dark brown solid: mp 308-310° C.; HRES(+) m/e calcd for $C_{20}H_{16}N_4OS$ $(M+H)^+$ 361.1118. found 361.1122.

Example 6

2-(1-(R)-Hydroxymethyl-2-methylpropylamino)-5-[1-(1H-pyrrolo[2,3-b]pyridin-3-yl)-meth-(Z)-ylidine]-thiazol-4-one

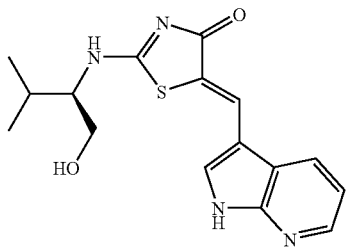

a) Preparation of 2-(1-(R)-hydroxymethyl-2-methyl-propylamino)-thiazol-4-one

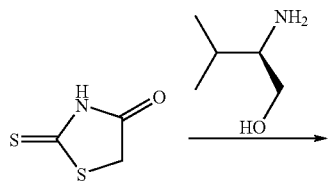

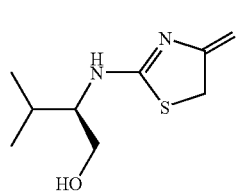

To a suspension of (R)-valinol (1 g, 9.69 mmol) and Rhodanine (1.3 g, 9.69 mmol) in acetonitrile (40 mL) was added DIPEA (5.06 mL, 29 mmol) at room temperature. Then, this solution was cooled to 0° C. and mercuric chloride (2.72 g, 10 mmol) was added in two portions within a period of 10 min. After addition, the suspension was allowed to warm to room temperature and stirred for 2 days. The resulting black solids were filtered through a plug of celite and washed with ethyl acetate (500 mL). The filtrate was removed under the vacuum and the crude residue was diluted with water (100 mL) and ethyl acetate (100 mL). The two layers were separated and the aqueous layer was extracted with ethyl acetate (2×50 mL). The combined organic extracts were washed with brine solution and dried over anhydrous magnesium sulfate. Filtration of the drying agent and removal of the solvent under the vacuum gave crude residue which was purified by using a Biotage silica gel column chromatography to obtain 0.82 g (42% yield) of 2-(1-(R)-hydroxymethyl-2-methylpropylamino)-thiazol-4-one was isolated as a white amorphous solid: EI-HRMS m/e calcd for $C_8H_{14}N_2O_2S$ (M$^+$) 202.0776. found 202.0778.

b) Preparation of 2-(1-(R)-hydroxymethyl-2-methyl-propylamino)-5-[1-(1H-pyrrolo[2,3,b]pyridin-3-yl)-meth-(Z)-ylidine]-thiazol-4-one

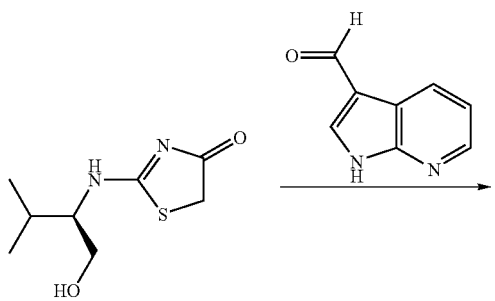

-continued

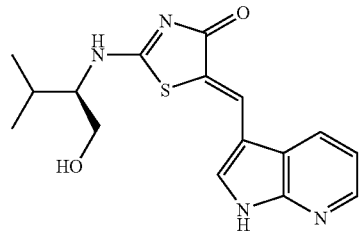

To a suspension of 2-(1-(R)-hydroxymethyl-2-methylpropylamino)-thiazol-4-one (70 mg, 0.35 mmol) and 1H-pyrrolo[2,3-b]pyridine-3-carbaldehyde (63 mg, 0.43 mmol) in toluene (700 uL) in a microwave tube was added benzoic acid (4.3 mg, 0.035 mmol) and piperidine (3.5 uL, 0.035 mmol) at room temperature. The microwave tube was sealed and heated to 150° C. in a closed microwave for 1 h. Then, the mixture was cooled to room temperature and diluted with toluene. The solids were collected by filtration and washed with toluene. The resulting solids were treated with dichloromethane and methanol to remove some color and other impurities. Filtration of the solids and drying in air afforded 14 mg (36.7% yield) of 2-(1-(R)-hydroxymethyl-2-methylpropylamino)-5-[1-(1H-pyrrolo[2,3-b]pyridin-3-yl)-meth-(Z)-ylidine]-thiazol-4-one as an yellow solid: mp 269-271° C.; HRES(+) m/e calcd for $C_{16}H_{18}N_4O_2S$ (M$^+$) 331.1223. found 331.1226.

Example 7

Acetic Acid 2-[4-oxo-5-(1H-pyrrolo[2,3,b]pyridine-3-ylmethylene)-4,5-dihydro-thiazol-2-ylamino]-2-(R)-phenyl-ethyl ester

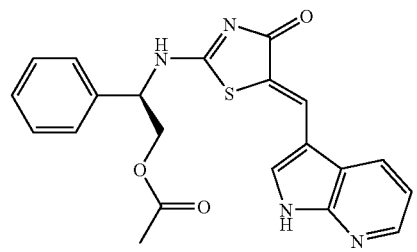

a) Preparation of Acetic Acid 2-[4-oxo-4,5-dihydro-thiazol-2-ylamino]-2-(R)-phenyl-ethyl ester

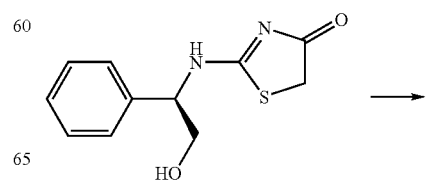

-continued

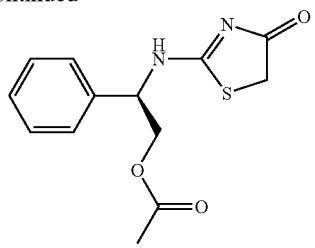

To a solution of 2-(2-(R)-hydroxy-1-phenyl-ethylamino)-thiazol-4-one (6.37 g, 26.9 mmol) in dichloromethane (200 mL) were added triethylamine (7.52 mL, 54 mmol) and then, acetyl chloride (2.3 mL, 32.28 mmol) at 5° C. After addition, the solution was allowed to warm to room temperature and stirred for 2 days. This solution was transferred to a separatory funnel and washed with brine solution and dried over anhydrous magnesium sulfate. Filtration of the drying agent and removal of the solvent under the vacuum gave the crude yellow oil which was purified by using a Biotage (40 m) silica gel column chromatography to afford 4.6 g (61.5% yield) of desired acetic acid 2-[4-oxo-4,5-dihydro-thiazol-2-ylamino]-2-(R)-phenyl-ethyl ester as a white amorphous solid: ES-LRMS m/e calcd for $C_{13}H_{14}N_2O_3S$ (M+) 279.33. found 279.1.

b) Preparation of Acetic Acid 2-[4-oxo-5-(1H-pyrrolo[2,3,b]pyridine-3-ylmethylene)-4,5-dihydro-thiazol-2-ylamino]-2-(R)-phenyl-ethyl ester

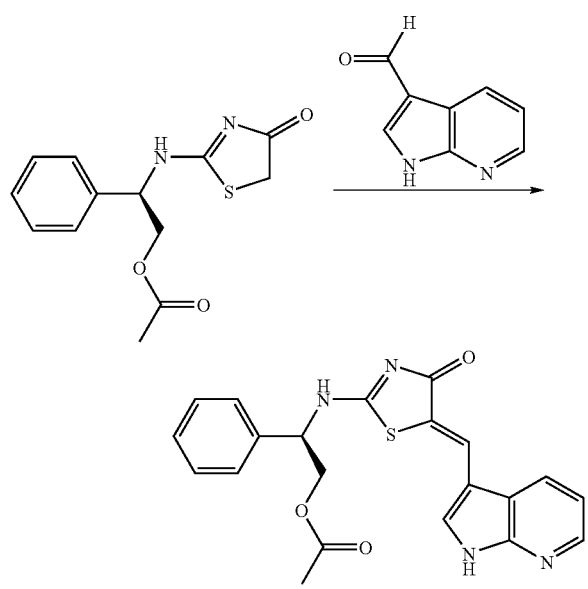

To a suspension of acetic acid 2-[4-oxo-4,5-dihydro-thiazol-2-ylamino]-2-(R)-phenyl-ethyl ester (400 mg, 1.43 mmol) and 1H-pyrrolo[2,3-b]pyridine-3-carbaldehyde (77.3 mg, 0.53 mmol) in toluene (5 mL) in a microwave tube was added benzoic acid (17.64 mg, 0.144 mmol) and piperidine (14.5 uL, 0.144 mmol) at room temperature. The microwave tube was sealed and heated to 150° C. in a closed microwave for 1 h. Then, the mixture was cooled to room temperature and diluted with toluene. The solids were collected by filtration and washed with toluene and dichloromethane. After drying in air, 313 mg (53.6% yield) of acetic acid 2-[4-oxo-5-(1H-pyrrolo[2,3,b]pyridine-3-ylmethylene)-4,5-dihydro-thiazol-2-ylamino]-2-(R)-phenyl-ethyl ester was isolated as a white solid: mp 243.7-246.8° C.; HRES(+) m/e calcd for $C_{21}H_{18}N_4O_3S$ (M+H)+ 407.1173. found 407.1172.

Example 8

2-(2-Chlorobenzylamino)-5-[1-(1H-pyrrolo[2,3-b]pyridin-3-yl)-meth-(Z)-ylidine]-thiazol-4-one

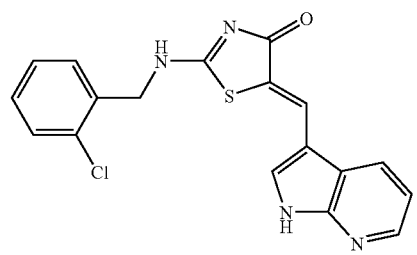

a) Preparation of 2-(2-chloro-benzylamino)-thiazol-4-one

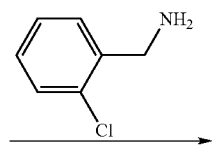

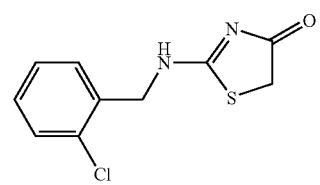

To a suspension of 2-chlorobenzylamine (7.88 g, 55 mmol) and Rhodanine (6.65 g, 50 mmol) in acetonitrile (150 mL) was added DIPEA (19.15 mL, 110 mmol) at room temperature. Then, this solution was cooled to 0° C. and mercuric chloride (13.5 g, 50 mmol) was added in three portions within a period of 15 min. After addition, the suspension was allowed to warm to room temperature and stirred for 3 days. The resulting black solids were filtered through a plug of celite and washed with dichloromethane (1 L) and methanol (500 mL). The combined solvents were removed under the vacuum and the crude residue was diluted with water (150 mL) and ethyl acetate (150 mL). After shaking, lot of solids formed which was collected by filtration to obtain 1.25 g of the desired product. Then, the two layers were separated and the ethyl acetate layer was washed with brine solution and dried over anhydrous magnesium sulfate. After filtration, the ethyl acetate solution was removed partially and then it was stored in the refrigerator. The resulting solids were collected by filtration to afford 2.67 g of the desired product. Then, the aqueous layer was extracted with dichloromethane (2×150 mL). The dichloromethane extracts were washed with brine solution and dried over anhydrous magnesium sulfate. Filtration of the drying agent and removal of the solvent under the vacuum gave the crude residue which was purified by using a Biotage (40 m) silica gel column chromatography to obtain 4.2 g (total product 8.12 g, 67.5% yield) of 2-(2-chlorobenzylamino)-thiazol-4-one as a white amorphous solid: EI-HRMS m/e calcd for $C_{10}H_9ClN_2OS$ (M+) 240.0124. found 240.0122.

b) Preparation of 2-(2-chlorobenzylamino)-5-[1-(1H-pyrrolo[2,3-b]pyridin-3-yl)-meth-(Z)-ylidine]-thiazol-4-one

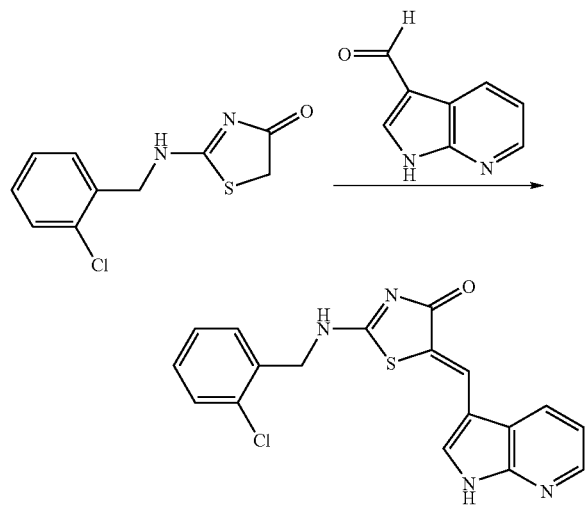

To a suspension of 2-(2-chlorobenzylamino)-thiazol-4-one (120 mg, 0.5 mmol) and 1H-pyrrolo[2,3-b]pyridine-3-carbaldehyde (88 mg, 0.6 mmol) in toluene (3 mL) in a microwave tube was added benzoic acid (7.5 mg, 0.06 mmol) and piperidine (5.9 uL, 0.06 mmol) at room temperature. The microwave tube was sealed and heated to 150° C. in a closed microwave for 30 min. Then, the mixture was cooled to room temperature and diluted with toluene. The solids were collected by filtration and washed with toluene. This was suspended in methanol (15 mL) and heated with heat gun. It was not dissolved completely, however it was cooled to room temperature and the solids were collected by filtration and washed with methanol. After drying in air, 175 mg (95% yield) of 2-(2-chlorobenzylamino)-5-[1-(1H-pyrrolo[2,3-b]pyridin-3-yl)-meth-(Z)-ylidine]-thiazol-4-one was isolated as an yellow solid. HRES(+) m/e calcd for $C_{18}H_{13}ClN_4OS$ (M+H)$^+$ 369.0572. found 369.0574.

Example 9

2-(2-Chloro-6-methylbenzylamino)-5-[1-(1H-pyrrolo[2,3-b]pyridin-3-yl)-meth-(Z)-ylidine]-thiazol-4-one

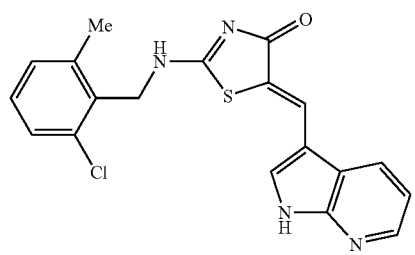

a) Preparation of 2-(2-chloro-6-methylbenzylamino)-thiazol-4-one

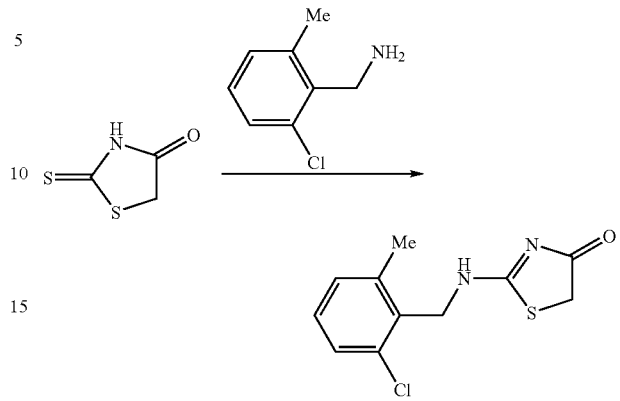

To a solution of 2-chloro-6-methylbenzylamine (650 mg, 4.2 mmol) and Rhodanine (559 mg, 4.2 mmol) in acetonitrile (25 mL) was added DIPEA (1.74 mL, 10 mmol) at room temperature. Then, this solution was cooled to 0° C. and mercuric chloride (1.22 g, 4.5 mmol) was added in one portion. After addition, the suspension was allowed to warm to room temperature and stirred for 3 days. The resulting black solids were filtered through a plug of celite and washed with dichloromethane (500 mL) and methanol (250 mL). The combined solvents were removed under the vacuum and the crude residue was dissolved in ethyl acetate (25 mL) at hot condition and stored in the refrigerator overnight. Then, the solids were collected by filtration and washed with ethyl acetate. After drying in air, 305 mg (28.5% yield) of 2-(2-chloro-6-methylbenzylamino)-thiazol-4-one was isolated as a white amorphous solid: EI-HRMS m/e calcd for $C_{11}H_{11}ClN_2OS$ (M$^+$) 254.0281. found 254.0282.

b) Preparation of 2-(2-chloro-6-methylbenzylamino)-5-[1-(1H-pyrrolo[2,3-b]pyridin-3-yl)-meth-(Z)-ylidine]-thiazol-4-one

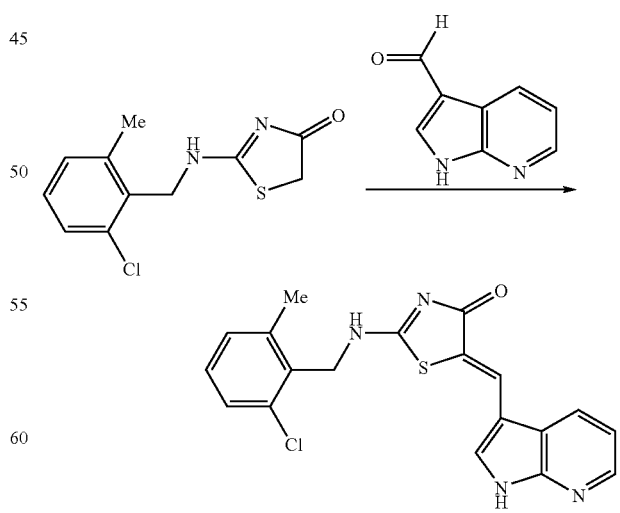

To a suspension of 2-(2-chloro-6-methylbenzylamino)-thiazol-4-one (63 mg, 0.25 mmol) and 1H-pyrrolo[2,3-b]pyridine-3-carbaldehyde (44 mg, 0.3 mmol) in toluene (2 mL) in a microwave tube was added benzoic acid (3.8 mg, 0.03 mmol) and piperidine (3 uL, 0.03 mmol) at room temperature. The microwave tube was sealed and heated to 150° C. in a closed microwave for 30 min. Then, the mixture was cooled to room temperature and diluted with toluene. The solids were collected by filtration and washed with toluene. These solids were suspended in methanol (10 mL) and heated with heat gun. Although, it was not dissolved completely, however, it was cooled to room temperature and the solids were collected by filtration and washed with methanol. After drying in air, 58 mg (61% yield) of 2-(2-chloro-6-methylbenzylamino)-5-[1-(1H-pyrrolo[2,3-b]pyridin-3-yl)-meth-(Z)-ylidine]-thiazol-4-one was isolated as a light green solid. HRES(+) m/e calcd for $C_{19}H_{15}ClN_4OS$ (M+H)$^+$ 383.0730. found 383.0728.

Example 10

2-[(3-Methyl-thiophen-2-ylmethyl)-amino)-5-[1-(1H-pyrrolo[2,3-b]pyridin-3-yl)-meth-(Z)-ylidine]-thiazol-4-one a) Preparation of 2-[(3-methyl-thiophen-2-ylmethyl)-amino]-thiazol-4-one To a solution of 3-methyl-thiophen-2-ylmethylamine (700 mg, 5.5 mmol) and Rhodanine (732 mg, 5.5 mmol) in acetonitrile (30 mL) was added DIPEA (1.91 mL, 11 mmol) at room temperature. Then, this solution was cooled to 0° C. and mercuric chloride (1.52 g, 5.6 mmol) was added in one portion. After addition, the suspension was allowed to warm to room temperature and stirred for 3 days. The resulting black solids were filtered through a plug of celite and washed with acetonitrile (200 mL) and ethyl acetate (250 mL). The combined solvents were removed under the vacuum and the crude residue was dissolved in dichloromethane (150 mL) and washed with water (100 mL) and brine solution. After drying over anhydrous magnesium sulfate, the filtrate was removed under the vacuum and the residue was dissolved in dichloromethane (10 mL) and diluted with hexanes (10 mL). After cooling in the refrigerator overnight, the solids were collected by filtration and washed with dichloromethane. After drying in air, 390 mg (31.5% yield) of 2-[(3-methyl-thiophen-2-ylmethyl)-amino]-thiazol-4-one was isolated as a light yellow amorphous solid: EI-HRMS m/e calcd for $C_9H_{10}N_2OS_2$ (M$^+$) 226.0235. found 226.0232.

b) Preparation of 2-[(3-methyl-thiophen-2-ylmethyl)-amino)-5-[1-(1H-pyrrolo[2,3-b]pyridin-3-yl)-meth-(Z)-ylidine]-thiazol-4-one

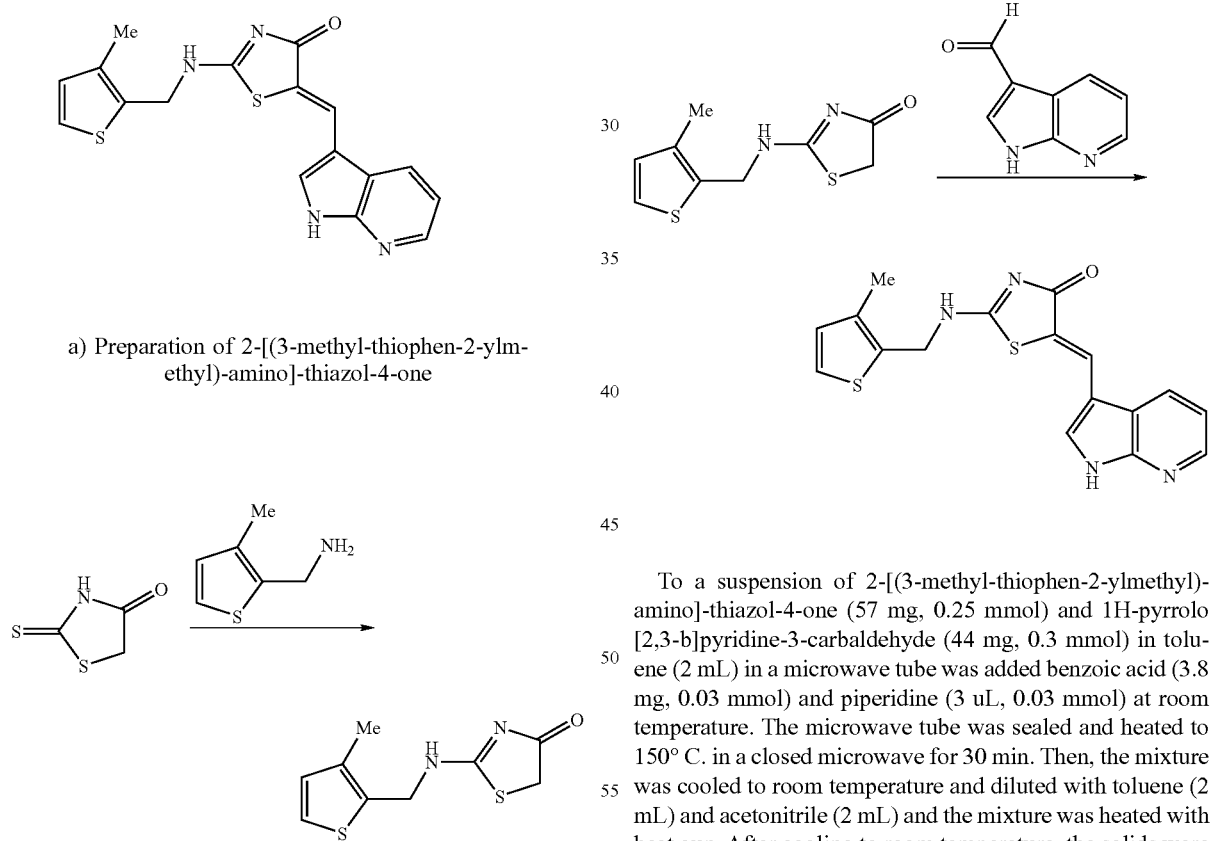

To a suspension of 2-[(3-methyl-thiophen-2-ylmethyl)-amino]-thiazol-4-one (57 mg, 0.25 mmol) and 1H-pyrrolo[2,3-b]pyridine-3-carbaldehyde (44 mg, 0.3 mmol) in toluene (2 mL) in a microwave tube was added benzoic acid (3.8 mg, 0.03 mmol) and piperidine (3 uL, 0.03 mmol) at room temperature. The microwave tube was sealed and heated to 150° C. in a closed microwave for 30 min. Then, the mixture was cooled to room temperature and diluted with toluene (2 mL) and acetonitrile (2 mL) and the mixture was heated with heat gun. After cooling to room temperature, the solids were collected by filtration and washed with toluene. These solids were suspended in methanol (10 mL) and heated with heat gun. After cooling to room temperature, the solids were collected by filtration and washed with methanol. After drying in air, 35 mg (39.5% yield) of 2-[(3-methyl-thiophen-2-ylmethyl)-amino)-5-[1-(1H-pyrrolo[2,3-b]pyridin-3-yl)-meth-(Z)-ylidine]-thiazol-4-one was isolated as an amorphous yellow solid. HRES(+) m/e calcd for $C_{17}H_{14}N_4OS$ (M+H)$^+$ 355.0682. found 355.0686.

Example 11

2-(2-Chloro-4-fluoro-benzylamino)-5-[1-(1H-pyrrolo[2,3-b]pyridin-3-yl)-meth-(Z)-ylidine]-thiazol-4-one

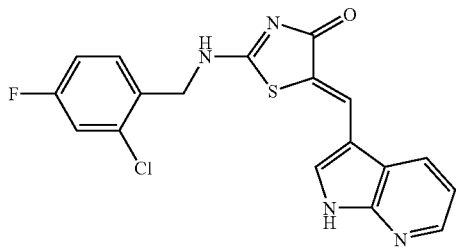

a) Preparation of 2-(2-chloro-4-fluoro-benzylamino)-thiazol-4-one

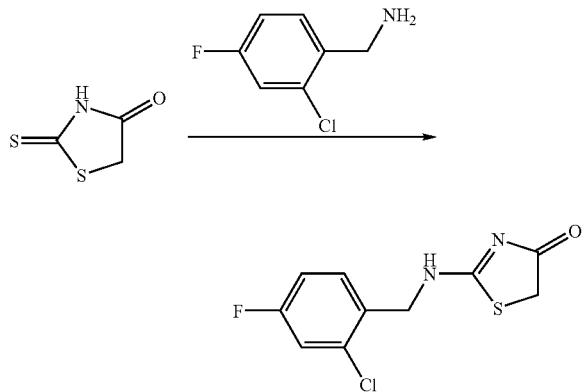

To a solution of 2-chloro-4-fluoro-benzylamine (4.5 g, 28.19 mmol) and Rhodanine (3.75 g, 28.2 mmol) in acetonitrile (170 mL) was added DIPEA (9.82 mL, 56.4 mmol) at room temperature. Then, this solution was cooled to 0° C. and mercuric chloride (8.42 g, 31.02 mmol) was added in two portions within 10 min. After addition, the suspension was allowed to warm to room temperature and stirred for 3 days. The resulting black solids were filtered through a plug of celite and washed with acetonitrile (1.0 L) and ethyl acetate (500 mL). The combined solvents were removed under the vacuum and the crude residue was dissolved in ethyl acetate (150 mL) and washed with water (100 mL) and brine solution (100 mL). After drying over magnesium sulfate, the filtrate was removed under the vacuum and the residue was dissolved in ethyl acetate (50 mL). After cooling in the refrigerator overnight, the solids were collected by filtration and washed with hexanes. After drying in air, 1.2 g (16.5% yield) of 2-(2-chloro-4-fluoro-benzylamino)-thiazol-4-one was isolated as a white amorphous solid: EI-HRMS m/e calcd for $C_{10}H_8FN_2OS_2$ (M+) 258.0030. found 258.0027.

b) Preparation of 2-(2-chloro-4-fluoro-benzylamino)-5-[1-(1H-pyrrolo[2,3-b]pyridin-3-yl)-meth-(Z)-ylidine]-thiazol-4-one

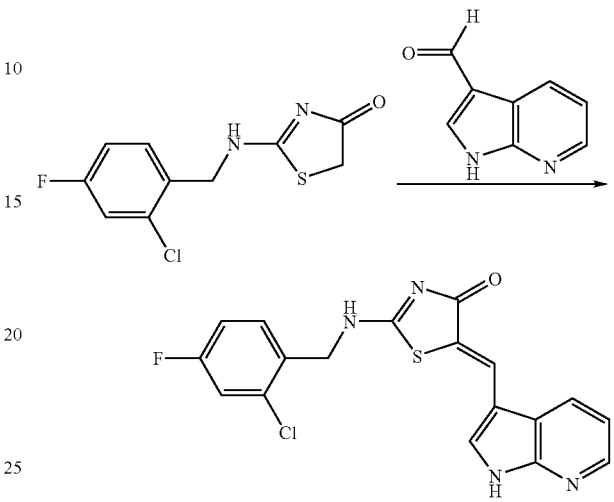

To a suspension of 2-(2-chloro-4-fluoro-benzylamino)-thiazol-4-one (130 mg, 0.5 mmol) and 1H-pyrrolo[2,3-b]pyridine-3-carbaldehyde (88 mg, 0.6 mmol) in toluene (4 mL) in a microwave tube was added benzoic acid (7.5 mg, 0.06 mmol) and piperidine (6 uL, 0.06 mmol) at room temperature. The microwave tube was sealed and heated to 150° C. in a closed microwave for 30 min. Then, the mixture was cooled to room temperature and diluted with toluene (2 mL) and acetonitrile (2 mL) and the mixture was heated with heat gun. After cooling to room temperature, the solids were collected by filtration and washed with toluene. These solids were dissolved in DMSO (5 mL) at hot condition and diluted with acetonitrile (25 mL). After cooling in the refrigerator overnight, the solids were collected by filtration and washed with acetonitrile. After drying in air, 69 mg (36% yield) of 2-(2-chloro-4-fluoro-benzylamino)-5-[1-(1H-pyrrolo[2,3-b]pyridin-3-yl)-meth-meth-(Z)-ylidine]-thiazol-4-one was isolated as an amorphous green solid. HRES(+) m/e calcd for $C_{18}H_{12}ClFN_4OS$ (M+H)+ 387.0477. found 387.0476.

Example 12

2-[(5-Methyl-pyrazin-2-ylmethyl)-amino]-5-[1-(1H-pyrrolo[2,3-b]pyridin-3-yl)-meth-(Z)-ylidine]-thiazol-4-one

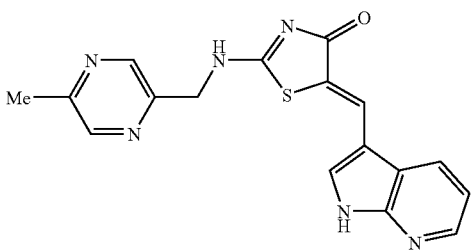

a) Preparation of 2-[(5-methyl-pyrazin-2-ylmethyl)-amino)-thiazol-4-one

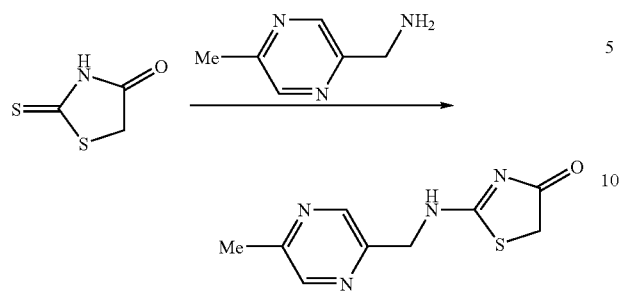

To a solution of 2-(aminomethyl)-5-methyl-pyrazine (3.69 g, 30 mmol) and Rhodanine (3.59 g, 27 mmol) in acetonitrile (100 mL) was added DIPEA (10.45 mL, 60 mmol) at room temperature. Then, this solution was cooled to 0° C. and mercuric chloride (8.15 g, 30 mmol) was added in two portions within 10 min. After addition, the suspension was allowed to warm to room temperature and stirred for 3 days. The resulting black solids were filtered through a plug of celite and washed with acetonitrile (1.0 L) and ethyl acetate (500 mL). The combined solvents were removed under the vacuum and the crude residue was dissolved in acetonitrile (25 mL) at hot condition. After cooling in the refrigerator overnight, the solids were collected by filtration and washed with acetonitrile. After drying in air, 1.5 g (25% yield) of 2-[(5-methyl-pyrazin-2-ylmethyl)-amino)-thiazol-4-one was isolated as a white solid: HRES(+) m/e calcd for $C_9H_{10}N_4OS$ (M+H)$^+$ 223.0648. found 223.0648.

b) Preparation of 2-[(5-methyl-pyrazin-2-ylmethyl)-amino]-5-[1-(1H-pyrrolo[2,3-b]pyridin-3-yl)-meth-(Z)-ylidine]-thiazol-4-one

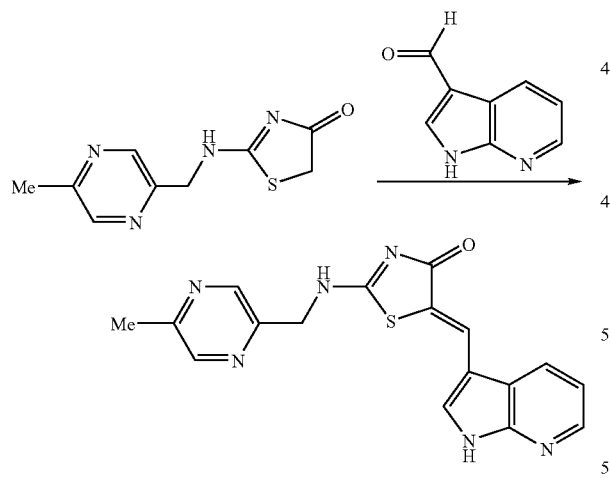

To a suspension of 2-[(5-methyl-pyrazin-2-ylmethyl)-amino)-thiazol-4-one (112 mg, 0.5 mmol) and 1H-pyrrolo[2,3-b]pyridine-3-carbaldehyde (88 mg, 0.6 mmol) in toluene (4 mL) in a microwave tube was added benzoic acid (7.5 mg, 0.06 mmol) and piperidine (6 uL, 0.06 mmol) at room temperature. The microwave tube was sealed and heated to 150° C. in a closed microwave for 30 min. Then, the mixture was cooled to room temperature and diluted with toluene (2 mL) and acetonitrile (2 mL) and the mixture was heated with heat gun. After cooling to room temperature, the solids were collected by filtration and washed with toluene. After drying in air, 80 mg (45.7% yield) of 2-[(5-methyl-pyrazin-2-ylmethyl)-amino]-5-[1-(1H-pyrrolo[2,3-b]pyridin-3-yl)-meth-(Z)-ylidine]-thiazol-4-one was isolated as an amorphous green solid. HRES(+) m/e calcd for $C_{17}H_{14}N_6OS$ (M+H)$^+$ 351.1023. found 351.1021.

Example 13

2-[2-(3-Fluoro-phenyl)-ethylamino]-5-[1-(1H-pyrrolo[2,3-b]pyridin-3-yl)-meth-(Z)-ylidine]-thiazol-4-one

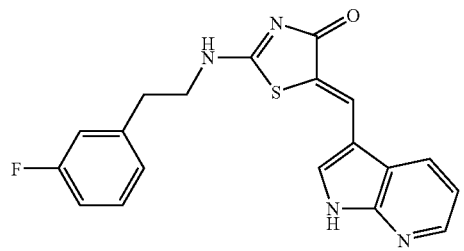

a) Preparation of 2-[2-(3-fluorophenyl)-ethylamino]-thiazol-4-one

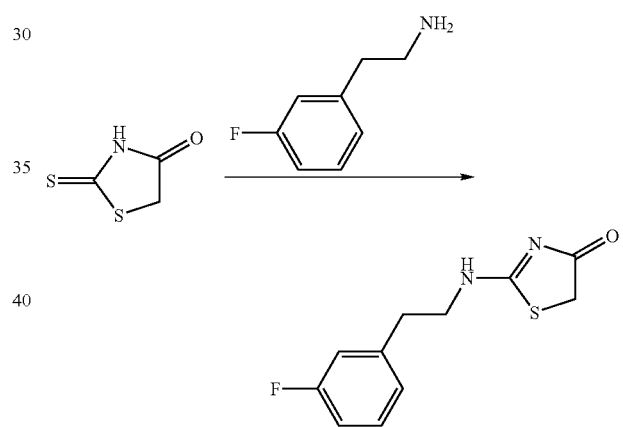

To a solution of 3-fluoro phenethylamine (3.06 g, 22 mmol) and Rhodanine (2.66 g, 20 mmol) in acetonitrile (70 mL) was added DIPEA (7.66 mL, 44 mmol) at room temperature. Then, this solution was cooled to 0° C. and mercuric chloride (5.97 g, 22 mmol) was added in two portions within 10 min. After addition, the suspension was allowed to warm to room temperature and stirred for 2 days. The resulting black solids were filtered through a plug of celite and washed with acetonitrile (1.0 L) and ethyl acetate (500 mL). The combined solvents were removed under the vacuum and the crude residue was dissolved in ethyl acetate (100 mL) and water (100 mL). The two layers were separated and the aqueous layer was extracted with ethyl acetate (2×100 mL). The combined extracts were washed with brine solution and dried over anhydrous magnesium sulfate. After filtration of the drying agent, the filtrate was removed under the vacuum and the crude residue was dissolved in acetonitrile (25 mL) at hot condition. After cooling in the refrigerator overnight, the solids were collected by filtration and washed with acetonitrile. After drying in air, 3.65 g (76.6% yield) of 2-[2-(3-fluoro-phenyl)-ethylamino]-thiazol-4-one was isolated as a white solid: HRES(+) m/e calcd for $C_{11}H_{11}FN_2OS$ (M+H)$^+$ 239.0649. found 239.0647.

b) Preparation of 2-[2-(3-fluoro-phenyl)-ethylamino]-5-[1-(1H-pyrrolo[2,3-b]pyridin-3yl)-meth-(Z)-ylidine]-thiazol-4-one

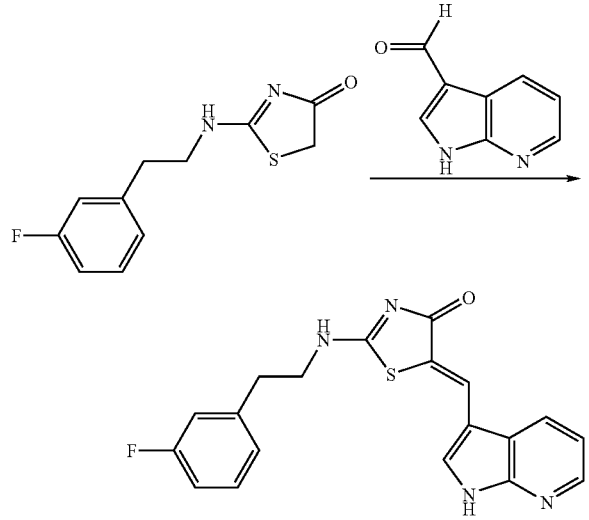

To a suspension of 2-[2-(3-fluoro-phenyl)-ethylamino]-thiazol-4-one (120 mg, 0.5 mmol) and 1H-pyrrolo[2,3-b]pyridine-3-carbaldehyde (88 mg, 0.6 mmol) in toluene (4 mL) in a microwave tube was added benzoic acid (7.5 mg, 0.06 mmol) and piperidine (6 uL, 0.06 mmol) at room temperature. The microwave tube was sealed and heated to 150° C. in a closed microwave for 30 min. Then, the mixture was cooled to room temperature and diluted with toluene (2 mL) and acetonitrile (2 mL) and the mixture was heated with heat gun. After cooling to room temperature, the solids were collected by filtration and washed with acetonitrile. After drying in air, 170 mg (93% yield) of 2-[2-(3-fluoro-phenyl)-ethylamino]-5-[1-(1H-pyrrolo[2,3-b]pyridin-3-yl)-meth-(Z)-ylidine]-thiazol-4-one was isolated as an yellow solid. HRES(+) m/e calcd for $C_{19}H_{15}FN_4OS$ (M+H)$^+$ 367.1024. found 367.1021.

Example 14

2-Cyclopropylamino-5-[1-(1H-pyrrolo[2,3-b]pyridin-3-yl)-meth-(Z)-ylidene]-thiazol-4-one

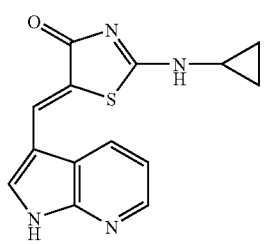

a) Preparation of 2-methylsulfanyl-5-(1H-pyrrolo[2,3-b]pyridin-3-ylmethylene)-thiazol-4-one

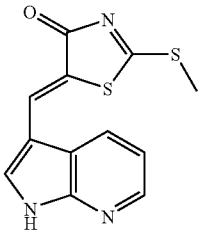

The suspension of 1H-pyrrolo[2,3-b]pyridine-3-carbaldehyde (example 1b, 1.2 g, 8.22 mmol), rhodanine (1.09 g, 8.22 mmol) and sodium acetate (2.69 g, 32.8 mmol) in acetic acid (12 mL) was stirred under reflux for 12 h. After cooling to room temperature, water (150 mL) was added. The solid was collected by filtration, washed with water and dried to obtain 5-(1H-pyrrolo[2,3-b]pyridin-3-ylmethylene)-2-thioxo-thiazolidin-4-one (2.2 g, 100%) as a brawn solid. LC-MS m/e 262 (MH$^+$).

The suspension of 5-(1H-pyrrolo[2,3-b]pyridin-3-ylmethylene)-2-thioxo-thiazolidin-4-one (2.2 g, 8.22 mmol), iodomethane (1.05 mL, 16.8 mmol) and DIEA (3.0 mL, 16.8 mmol) in anhydrous ethanol (110 mL) was stirred at 100° C. for 2 h. After adding water (200 mL), the solid was collected by filtration, washed with water and dried to obtain 2-methylsulfanyl-5-(1H-pyrrolo[2,3-b]pyridin-3-ylmethylene)-thiazol-4-one (1.48 g, 60.8%) as a grey solid. LC-MS m/e 276 (MH$^+$).

b) Preparation of 2-methylsulfanyl-5-(1H-pyrrolo[2,3-b]pyridin-3-ylmethylene)-thiazol-4-one The suspension of 2-methylsulfanyl-5-(1H-pyrrolo[2,3-b]pyridin-3-ylmethylene)-thiazol-4-one (55 mg, 02 mmol, example 14a), cyclopropylamine (23 mg, 0.4 mmol) and diisopropylethylamine (DIEA) (70 uL, 0.4 mmol) in acetonitrile (1.0 mL) was stirred under at 80° C. for 12 h. After cooling to room temperature, the solid was collected by filtration, washed with a little bit of acetonitrile and dried. Flash chromatography (Merck Silica gel 60, 230-400 mesh, 0%-10% methanol in methylene chloride in 30 min) afforded 2-cyclopropylamino-5-[1-(1H-pyrrolo[2,3-b]pyridin-3-yl)-meth-(Z)-ylidene]-thiazol-4-one (40 mg, 71%) as a light yellow solid. LC-MS m/e 285 (MH$^+$).

Example 15

2-Amino-5-[1-(1H-pyrrolo[2,3-b]pyridin-3-yl)-meth-(Z)-ylidene]-thiazol-4-one

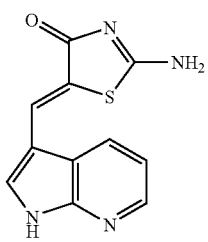

The suspension of 1H-pyrrolo[2,3-b]pyridine-3-carbaldehyde (example 1b, 200 mg, 1.4 mmol), pseudothiohydantoin (159 mg, 1.4 mmol), and sodium acetate (459 mg, 5.6 mmol) in acetic acid (2 mL) was stirred under reflux for 12 h. After cooling to room temperature, water was added. The solid was collected by filtration, washed with water and dried to obtain 2-amino-5-[1-(1H-pyrrolo[2,3-b]pyridin-3-yl)-meth-(Z)-ylidene]-thiazol-4-one (280 mg, 82%) as a slight yellow solid. LC-MS m/e 245 (MH$^+$).

Example 16

2-((R)-1-Hydroxymethyl-3-methyl-butylamino)-5-[1-(1H-pyrrolo[2,3-b]pyridin-3-yl)-meth-(Z)-ylidene]-thiazol-4-one

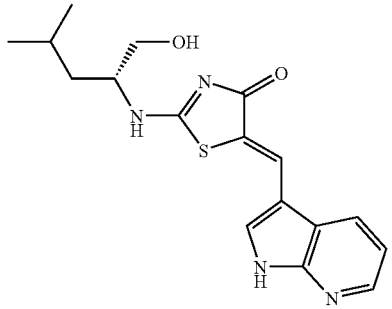

Similar procedure as described in Example 14b was used, starting from 2-methylsulfanyl-5-(1H-pyrrolo[2,3-b]pyridin-3-ylmethylene)-thiazol-4-one (Example 14a), 2-((R)-1-Hydroxymethyl-3-methyl-butylamine and DIEA to give 2-((R)-1-hydroxymethyl-3-methyl-butylamino)-5-[1-(1H-pyrrolo[2,3-b]pyridin-3-yl)-meth-(Z)-ylidene]-thiazol-4-one. LC-MS m/e 345 (MH$^+$).

Example 17

2-[(R)-1-(4-Fluoro-phenyl)-2-hydroxy-ethylamino]-5-[1-(1H-pyrrolo[2,3-b]pyridin-3-yl)-meth-(Z)-ylidene]-thiazol-4-one

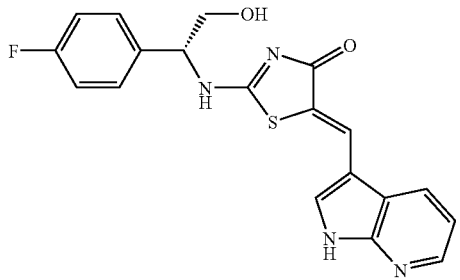

a) Preparation of (R)-2-(4-fluoro-phenyl)-1-hydroxymethyl-ethylamine

To the solution of sodium borohydride (0.54 g, 14.2 mmol) in THF (10 mL) was added D-4-Fluorophenylglycine (1.0 g, 5.9 mmol). After cooling to 0° C., the solution of iodine (1.5 g, 5.9 mmol) in THF (10 mL) was added dropwisely. The mixture was stirred at reflux for 18 h. after cooling to the room temperature, methanol (7 mL) was added to stop the reaction. After removal of solvent, 20% potassium hydroxide (50 mL) was added. The mixture was stirred for 4 h and extracted with methylene chloride (3×50 mL). The combined organic layers were dried over sodium sulfate, filtered, and concentrated in vacuo. Flash chromatography (Merck Silica gel 60, 70-230 mesh, 0%-10% methanol in 0%-5% methanol in methylene chloride in 30 min afforded (R)-2-(4-fluoro-phenyl)-1-hydroxymethyl-ethylamine (0.63 g, 69%).

b) Preparation of 2-[(R)-1-(4-fluoro-phenyl)-2-hydroxy-ethylamino]-5-[1-(1H-pyrrolo[2,3-b]pyridin-3-yl)-meth-(Z)-ylidene]-thiazol-4-one Then similar procedure as described in example 14b was used, starting from 2-methylsulfanyl-5-(1H-pyrrolo[2,3-b]pyridin-3-ylmethylene)-thiazol-4-one (example 14a), 2-[(R)-1-(4-fluoro-phenyl)-2-hydroxy-ethylamine and DIEA to give 2-[(R)-1-(4-fluoro-phenyl)-2-hydroxy-ethylamino]-5-[1-(1H-pyrrolo[2,3-b]pyridin-3-yl)-meth-(Z)-ylidene]-thiazol-4-one. LC-MS m/e 383 (MH$^+$).

Example 18

2-(2-Methoxy-phenylamino)-5-[1-(1H-pyrrolo[2,3-b]pyridin-3-yl)-meth-(Z)-ylidene]-thiazol-4-one

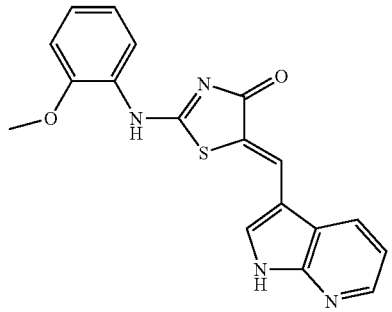

Similar procedure as described in example 14b was used, starting from 2-methylsulfanyl-5-(1H-pyrrolo[2,3-b]pyridin-3-ylmethylene)-thiazol-4-one (example 14a), 2-(2-methoxy-phenylamine and DIEA to give 2-(2-methoxy-phenylamino)-5-[1-(1H-pyrrolo[2,3-b]pyridin-3-yl)-meth-(Z)-ylidene]-thiazol-4-one. LC-MS m/e 351 (MH$^+$).

Example 19

The pharmacological properties of the compounds of this invention may be confirmed by a number of pharmacological assays. The exemplified pharmacological assays which follow have been carried out with the compounds according to the invention and their salts. The compounds of the invention exhibited CDK1/Cyclin B and CDK2/Cyclin E activity with Ki values of less than 5.0 μM. This demonstrates that all of these compounds were active to inhibit CDK1/Cyclin B and CDK2/Cyclin E.

Kinase Assays

To determine inhibition of CDK1 activity, either Flash-Plate™ (NEN™-Life Science Products) assay or HTRF assay was performed. Both types of kinase assays were carried out using recombinant human CDK1/Cyclin B complex. GST-cyclinB (GST-cycB) and CDK1 cDNA clones in baculovirus vectors were provided by Dr. W. Harper at the Baylor College of Medicine, Houston, Tex. Proteins were co-expressed in High Five™ insect cells and the complex was purified on glutathione Sepharose resin (Pharmacia, Piscataway, N.J.) as previously described (Harper, J. W. et al. Cell 1993, 75, 805-816). A 6x-Histidine tagged truncated form of retinoblastoma (Rb) protein (amino acid 386-928) was used as the substrate for the CDK1/Cyclin B assay (the expression plasmid was provided by Dr. Veronica Sullivan, Department of Molecular Virology, Roche Research Centre, Welwyn Garden City, United Kingdom). The Rb protein is a natural substrate for phosphorylation by CDK1 (see Herwig and Strauss Eur. J. Biochem. Vol. 246 (1997) pp. 581-601 and the references cited therein). The expression of the 62Kd protein was under the control of an IPTG inducible promoter in an M15 E. coli strain. Cells were lysed by sonication and purification was carried out by binding lysates at pH 8.0 to a Ni-chelated agarose column pretreated with 1 mM imidazole. The resin was then washed several times with incrementally decreasing pH buffers to pH 6.0, and eluted with 500 mM imidazole. Eluted protein was dialyzed against 20 mM HEPES pH 7.5, 30% glycerol, 200 mM NaCl, and 1 mM DTT. Purified Rb fusion protein stocks were quantitated for protein concentration, aliquoted, and stored at −70° C.

For the FlashPlate kinase assay, 96-well FlashPlates were coated with Rb protein at 10 µg/ml, using 100 µl per well. Plates were incubated at 4° C. overnight or at room temperature for 3 hours on a shaker. To control for nonspecific phosphorylation, one row of wells was coated with 100 µl/well coating buffer (20 mM HEPES, 0.2 M NaCl). Plates were then washed twice with wash buffer (0.01% Tween 20 in phosphate-buffered saline). Compounds to be tested ("test compounds") were added to the wells at 5× final concentration. Reactions were initiated by immediate addition of 40 µl reaction mix (25 mM HEPES, 20 mM MgCl$_2$, 0.002% Tween 20, 2 mM DTT, 1 µM ATP, 4 nM 33P-ATP) and a sufficient amount of enzyme to give counts that were at least 10-fold above background. Plates were incubated at room temperature on a shaker for 30 minutes. Plates were washed four times with the wash buffer, sealed, and counted on the TopCount scintillation counter (Packard Instrument Co., Downers Grove, Ill.]. The percent inhibition of Rb phosphorylation, which is a measure of the inhibition of CDK activity, was determined according to the following formula:

$$100 \times \frac{1 - \text{test compound} - \text{nonspecific}}{\text{total} - \text{nonspecific}}$$

where "test compound" refers to the average counts per minute of the test duplicates, "nonspecific" refers to the average counts per minute when no CDK1/Cyclin B, etc., was added, and "total" refers to the average counts per minute when no compound was added. The IC$_{50}$ value is the concentration of test compound that reduces by 50% the protein-kinase induced incorporation of the radiolabel under the test conditions described. The value of the inhibitor constant Ki is calculated by the following: Ki=IC50/(1+[S]/Km), where [S] is the ATP concentration and Km is Michaelis constant.

The Homogeneous Time Resolved Fluorescence (HTRF) kinase assay was carried out in 96-well polypropylene plates (BD Biosciences, Bedford, Mass.). Test compounds were first dissolved in DMSO, and then diluted in kinase assay buffer 1 (25 mM HEPES, pH7.0, 8 mM MgCl$_2$, 1.5 mM DTT, and 162 µM ATP) with DMSO concentration at 15%. The CDK1/Cyclin B enzyme was diluted in kinase assay buffer 2 (25 mM HEPES, pH 7.0, 8 mM MgCl$_2$, 0.003% Tween 20, 0.045% BSA, 1.5 mM DTT, and 0.675 µM Rb protein). To initiate the kinase reaction, 20 µL of compound solution was mixed with 40 µL of CDK1/Cyclin B solution in assay plates with final concentration of CDK1/Cyclin B and Rb at 0.1 µg/mL and 0.225 µM, respectively, and incubated at 37° C. for 30 min. 15 µL of anti-phospho-Rb (Ser 780) antibody (Cell Signaling Technology, Beverly, Mass.) was added with a 1:7692 dilution of the antibody. Incubation was continued at 37° C. for 25 min, after which LANCE Eu-W1024 labeled anti-rabbit IgG (1 nM, PerkinElmer, Wellesley, Mass.) and anti-His antibody conjugated to SureLight-Allophucocyanin (20 nM, PerkinElmer, Wellesley, Mass.) were added to the wells. Incubation was continued at 37° C. for another 40 min. At the completion of the incubation, 35 µL of reaction mixture was transferred to fresh 384-well black polystyrene plates (Corning Incorporated, Corning, N.Y.) and read on a fluorescent plate reader at excitation wavelength of 340 nm and emission wavelength of 665/615 nm.

To determine the inhibition of CDK2 activity, similar procedure as described above in CDK1/Cyclin B assay was used for CDK2/Cyclin E activity except that CDK2/Cyclin E complex was used in the assay.

Ki values showing CDK1/Cyclin B and CDK2/Cyclin E activities that applied to compounds of the subject matter of this invention ranges from about 0.001 µM to about 5.000 µM. Specific data for some examples are as follows:

| Example | CDK1, Ki (µM) | CDK2, Ki (µM) |
|---------|---------------|---------------|
| 5       | 0.010         | 0.017         |
| 10      | 0.048         | 0.018         |
| 15      | 0.83          | 0.252         |
| 18      | 1.15          | 0.187         |

The invention claimed is:

1. A compound of the formula:

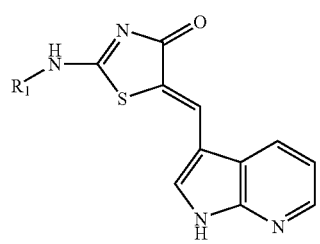

I wherein
R$_1$ is selected from hydrogen, lower alkyl, hydroxy-lower alkyl, cyclo-lower alkyl, lower alkoxy-lower alkyl and R$_2$—(X)n; where n is an integer from 0 to 1; X is selected from lower alkylene, hydroxy-loweralkylene, cyclo-loweralkylene, lower alkoxy-lower alkylene and lower alkanoyloxy-lower alkylene;

$R_2$ is

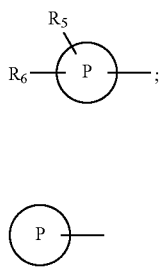

is selected from an aryl ring, a 4 to 6 membered heterocycloalkyl ring containing from 3 to 5 carbon atoms and from 1 to 2 hetero atoms selected from the group consisting of oxygen, nitrogen and sulfur; and a 5 or 6 membered heteroaromatic ring containing from 1 to 2 hetero atoms selected from the group consisting of oxygen, sulfur and nitrogen;

$R_5$ and $R_6$ are independently selected from the group consisting of hydroxy, hydroxy-lower alkyl, hydrogen, lower alkyl, halogen, perfluro lower alkyl and lower alkoxy, and n is an integer from 0 to 1; and pharmaceutically acceptable salts thereof.

2. The compound of claim 1 wherein said compound is:

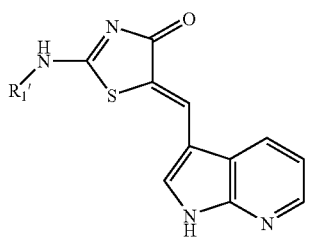

I-A wherein $R_1'$ is selected from hydrogen, lower alkyl, hydroxy lower alkyl, lower alkoxy-lower alkyl and cyclo-lower alkyl; and pharmaceutically acceptable salts thereof.

3. The compound of claim 2 wherein $R_1'$ is hydrogen or lower alkyl.

4. The compound of claim 3 wherein said compound is 2-amino-5-[1-(1H-pyrrolo[2,3-b]pyridin-3-yl)-meth-(Z)-ylidene]-thiazol-4-one.

5. The compound of claim 3 wherein $R_1'$ is cyclo-lower alkyl.

6. The compound of claim 5 wherein said compound is 2-cyclopropylamino-5-[1-(1H-pyrrolo[2,3-b]pyridin-3-yl)-meth-(Z)-ylidene]-thiazol-4-one.

7. The compound of claim 2 wherein $R_1'$ is hydroxy-lower alkyl or lower alkoxy lower alkyl.

8. The compound of claim 7 wherein said compound is 2-((R)-1-hydroxymethyl-3-methyl-butylamino)-5-[1-(1H-pyrrolo[2,3-b]pyridin-3-yl)-meth-(Z)-ylidene]-thiazol-4-one.

9. The compound of claim 7 wherein said compound is 2-(1-(R)-hydroxymethyl-2-methylpropylamino)-5-[1-(1H-pyrrolo[2,3-b]pyridin-3-yl)-meth-(Z)-ylidene]-thiazol-4-one.

10. The compound of claim 1 wherein said compound has the formula:

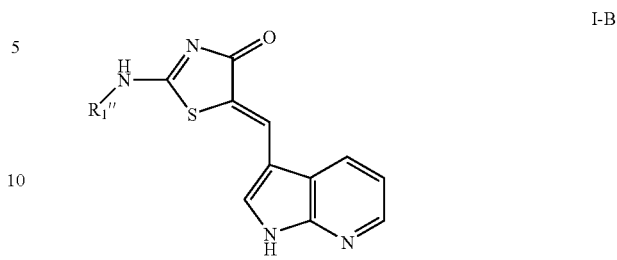

I-B wherein $R_1''$ is $R_2-(X)_n-$.

11. The compound of claim 10 wherein aryl is phenyl.

12. The compound of claim 11 wherein n is 1.

13. The compound of claim 12 wherein X is cyclo-lower alkylene.

14. The compound of claim 13 wherein said cyclo lower alkylene is cyclopropylene.

15. The compound of claim 14 wherein $R_2$ is

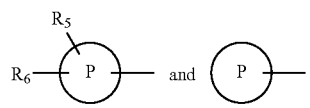

is phenyl.

16. The compound of claim 15 wherein said compound is 2-((1R,2S)-2-phenyl-cyclopropylamino)-5-[1-(1H-pyrrolo[2,3-b]pyridin-3-yl)-meth-(Z)-ylidene]-thiazol-4-one.

17. The compound of claim 12 wherein X is lower alkanoyloxy-lower alkylene.

18. The compound of claim 17 wherein $R_2$ is

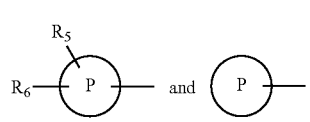

is phenyl.

19. The compound of claim 18 wherein said compound is acetic acid 2-[4-oxo-5-(1H-pyrrolo[2,3,b]pyridine-3-ylmethylene)-4,5-dihydro-thiazol-2-ylamino]-2-(R)-phenyl-ethyl ester.

20. The compound of claim 12 wherein X is lower alkylene.

21. The compound of claim 20 wherein $R_2$ is

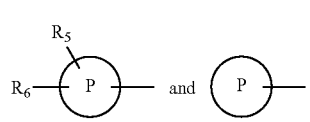

is phenyl.

22. The compound of claim 21 wherein $R_5$ and $R_6$ are hydrogen.

23. The compound of claim 21 wherein $R_6$ is independently halogen, trifluoromethyl, or lower alkyl and $R_6$ is hydrogen halogen, trifluoromethyl or lower alkyl.

24. The compound of claim 23 wherein said compound is 2-(2-chlorobenzylamino)-5-[1-(1H-pyrrolo[2,3-b]pyridin-3-yl)-meth-(Z)-ylidine]-thiazol-4-one.

25. The compound of claim 23 wherein said compound is 2-(2-chloro-6-methylbenzylamino)-5-[1-(1H-pyrrolo[2,3-b]pyridin-3-yl)-meth-(Z)-ylidine]-thiazol-4-one.

26. The compound of claim 23 wherein said compound is 2-(3-chloro-4-fluorobenzylamino)-5-[1-(1H-pyrrolo[2,3-b]pyridin-3-yl)-meth-(Z)-ylidine]-thiazol-4-one.

27. The compound of claim 23 wherein said compound is 2-(2-chloro-4-fluoro-benzylamino)-5-[1-(1H-pyrrolo[2,3-b]pyridin-3-yl)-meth-(Z)-ylidine]-thiazol-4-one.

28. The compound of claim 23 wherein said compound is 2-[2-(3-fluoro-phenyl)-ethylamino]-5-[1-(1H-pyrrolo[2,3-b]pyridin-3-yl)-meth-(Z)-ylidine]-thiazol-4-one.

29. The compound of claim 20 wherein $R_2$ is

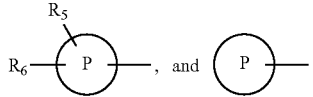

is a heteroaromatic ring containing from 1 to 2 hetero atoms selected from the group consisting of oxygen, nitrogen and sulfur.

30. The compound of claim 29 wherein said heteroaromatic ring contains 1 hetero atom.

31. The compound of claim 30 wherein said heteroatom is sulfur.

32. The compound of claim 30 wherein $R_5$ and $R_6$ are hydrogen or lower alkyl.

33. The compound of claim 32 wherein said compound is 5-[1-(1H-pyrrolo[2,3-b]pyridin-3-yl)-meth-(Z)-ylidine]-2-[(thiophen-2-yl-methyl)-amino]-thiazol-4-one.

34. The compound of claim 32 wherein said compound is 2-[(3-methyl-thiophen-2-ylmethyl)-amino]-5-[1-(1H-pyrrolo[2,3-b]pyridin-3-yl)-meth-(Z)-ylidine]-thiazol-4-one.

35. The compound of claim 29 wherein said heteroaromatic ring contains two hetero atoms.

36. The compound of claim 34 wherein both of said hetero atoms are nitrogen.

37. The compound of claim 36 wherein $R_5$ and $R_6$ are individually selected from the group consisting of hydrogen and lower alkyl.

38. The compound of claim 37 wherein said compound is 2-[(5-methyl-pyrazin-2-ylmethyl)-amino]-5-[1-(1H-pyrrolo[2,3-b]pyridin-3-yl)-meth-(Z)-ylidine]-thiazol-4-one.

39. The compound of claim 12 wherein X is hydroxy loweralkylene.

40. The compound of claim 39 wherein $R_2$ is

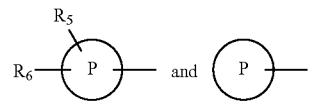

is phenyl.

41. The compound of claim 40 wherein $R_5$ and $R_6$ are individually selected from halogen, trifluorometyl, hydrogen and lower alkyl.

42. The compound of claim 41 wherein said compound is 2-(2-hydroxy-1-(R)-phenyl-ethylamino)-5-[1-(1H-pyrrolo[2,3-b]pyridin-3-yl)-meth-(Z)-ylidine]-thiazol-4-one.

43. The compound of claim 41 wherein said compound is 2-[(R)-1-(4-fluoro-phenyl)-2-hydroxy-ethylamino]-5-[1-(1H-pyrrolo[2,3-b]pyridin-3-yl)-meth-(Z)-ylidene]-thiazol-4-one.

44. The compound of claim 11 wherein n is 0 and $R_2$ is

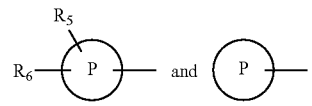

is phenyl.

45. The compound of claim 44 wherein $R_5$ and $R_6$ are individually selected from hydrogen, lower alkyl and lower alkoxy.

46. The compound of claim 45 wherein said compound is 2-(2-methoxy-phenylamino)-5-[1-(1H-pyrrolo[2,3-b]pyridin-3-yl)-meth-(Z)-ylidene]-thiazol-4-one.

* * * * *